United States Patent
Szyf et al.

(10) Patent No.: US 6,268,137 B1
(45) Date of Patent: Jul. 31, 2001

(54) SPECIFIC INHIBITORS OF DNA METHYL TRANSFERASE

(75) Inventors: Moshe Szyf, Cote St. Luc (CA); Pascal Bigey, Clermont-Ferrand (FR)

(73) Assignee: Methylgene, Inc., Quebec (CA)

( * ) Notice: Subject to any disclaimer, the term of this patent is extended or adjusted under 35 U.S.C. 154(b) by 0 days.

(21) Appl. No.: 09/206,866

(22) Filed: Dec. 8, 1998

Related U.S. Application Data

(63) Continuation-in-part of application No. 09/194,284, filed as application No. PCT/IB97/00879 on May 22, 1997, now abandoned, which is a continuation-in-part of application No. 08/653,954, filed on May 22, 1996, now abandoned.
(60) Provisional application No. 60/069,812, filed on Dec. 17, 1997.

(51) Int. Cl.[7] .............................. C07H 21/04; C12Q 1/68; C12N 15/09

(52) U.S. Cl. .............................. 435/6; 435/375; 435/455; 536/23.1; 536/24.1; 536/24.5

(58) Field of Search .......................... 435/6, 375; 514/44; 536/23.1, 24.1, 24.5

(56) References Cited

U.S. PATENT DOCUMENTS

| 5,503,975 | 4/1996 | Smith et al. .............................. 435/6 |
| 5,578,716 | 11/1996 | Szyf et al. .......................... 536/24.5 |

FOREIGN PATENT DOCUMENTS

| WO 92/06985 | 4/1992 | (WO) . |
| WO 95/15373 | 6/1995 | (WO) . |
| WO 95/15378 | 6/1995 | (WO) . |

OTHER PUBLICATIONS

Bigey et al. "Modified Oligonucleotides as Bona Fide Antagonists of Proteins Interacting with DNA" The Journal of Biological Chemistry vol. 274(8): 4594–4606, Feb. 19, 1999.*

Branch A. "A Good Antisense Molecule is Hard to Find" TIBS vol. 23:45–50, Feb. 1998.*

Koziolkiewicz et al. "Application of Phophate–Backbone–Modified Oligonucleotides in the Studies on EcoR1 Endonuclease Mechanism of Action" Biochemistry vol. 31:9460–9466, 1992.*

Stull et al. "Antigene, Ribozyme and Aptamer Nucleic Acid Drugs: Progress and Prospects" Pharmaceutical Research vol. 12(4):465–483, 1995.*

Bartolomei et al., "Epigenetic mechanisms underlying the imprinting of the mouse H19 gene," Genes Dev., vol. 7(Sep. 1993) pp. 1663–1673.

Brandeis et al., "The ontogeny of allele–specific methylation associated with imprinted genes in the mouse," EMBO J., vol. 12 (Sep. 1993) pp. 3669–3677.

Freedman et al., "Cellular tumorigenicity in nude mice: correlation with cell growth in semi–solid medium," Cell vol. 3 (Dec. 1974) pp. 355–359.

Friedman, S. et al., "Binding of the EcoRII methyltransferase to 5–fluorocytosine–containing DNA. Isolation of a bound peptide"; Nucleic Acids Research, vol. 20, No. 12 (1992) pp. 3241–3248.

(List continued on next page.)

Primary Examiner—Robert A. Schwartzman
Assistant Examiner—Sean McGarry
(74) Attorney, Agent, or Firm—Hale and Dorr LLP

(57) ABSTRACT

The invention provides novel mechanism-based inhibitors of DNA methyltransferase enzyme, and diagnostic and therapeutic uses for the same. The novel inhibitors according to the invention form stable, noncovalent complexes with DNA methyltransferase enzyme in a manner which is independent of S-adenosylmethionine.

9 Claims, 13 Drawing Sheets

BINDING OF HUMAN DNA METHYLTRANSFERASE TO DNA METHYLTRANSFERASE INHIBITORS

OTHER PUBLICATIONS

Holliday, R., "DNA methylation and epigenetic inheritance" Philos. Trans. R. Soc. Lond. B. Biol. Sci., vol. 326 (Jan. 1990) pp. 329–338.

Hopkin, K., "Move Over, Mutations: DNA Methylation May Drive Cancer, Too," The Journal of NIH Research, vol. 7 (Jul. 1995) pp. 26–28.

Ingraham et al., "A family of POU–domain and Pit–1 tissue–specific transcription factors in pituitary and neuroendocrine development," Annual Review of Physiology, vol. 52 (1990) pp. 773–791.

Kim, S.C. et al., "A novel gene–fusing vector: construction of a 5'–GGmCC–specific chimeric methyltransferase, M.BspR/M.BsuRI", Gene, vol. 100 (1991) pp. 45–50.

Lock et al., "Methylation of the Hprt gene on the inactive X occurs after chromosome inactivation," Cell, vol. 48 (Jan. 1987) pp. 39–46.

Maniatis et al., "Regulation of inducible and tissue–specific gene expression," Science, vol. 236 (Jun. 1987) pp. 1237–1245.

Midgeon, "X–chromosome inactivation: molecular mechanisms and genetic consequences", Trends Genet., vol. 10 (Jul. 1994) pp. 230–235.

Peterson et al., "Imprinting the genome: imprinted genes, imprinting genes, and a hypothesis for their interaction," Annu. Rev. Genet., vol. 27 (1993) pp. 7–31.

Pon, R.T., "Solid–phase supports for oligonucleotide synthesis," Methods in Molec. Biol., vol. 20 (1993) pp. 465–479.

Szyf et al., "Induction of myogenic differentiation by an expression vector encoding the DNA methyltransferase cDNA sequence in the antisense orientation." J. Biol. Chem., vol. 267 (Jun. 1992) pp. 12831–12836.

Szyf et al., "Ras induces a general DNA demethylation activity in mouse embryonal P19 cells," J. Biol. Chem., vol. 270 (May 1995) pp. 12690–12695.

Timinskas, A. et al., "Sequence motifs characteristic for DNA [cytosine–N4] and DNA [adenine–N6] methyltransferases. Classification of all DNA methyltransferases", Gene, vol. 157 (1995), pp. 3–11.

Uhlmann et al., "Antisense Oligonucleotides: A New Therapeutic Approach," Chemical Reviews, vol. 90(4) (Jun. 1990) pp. 543–584.

Osterman et al. "5–Fluorocytosine in DNA is a Mechanism–Based Inhibitor of HhaI Methylase," Biochemistry, vol. 27 (Jul. 12, 1988) pp. 5204–5210.

* cited by examiner

LABELED OLIGONUCLEOTIDE:      C      U      I

COLD OLIGONUCLEOTIDE:   − C U I   − C U I   − C U I

190kDa →

COLD OLIGONUCLEOTIDE:      C      U      I      HM

LABELED OLIGONUCLEOTIDE: − C U I   − C U I   − C U I   U I

190kDa →

TIME POST TREATMENT:   6    9    24   30
OLIGONUCLEOTIDE:      C U I  C U I  C U I  C U I

1h

4h

24h

SPECIFIC INHIBITORS OF DNA METHYL TRANSFERASE

This application claims the benefit of U.S. provisional application No. 60/069,812, filed Dec. 17, 1997. This application is also a continuation-in-part of U.S. Ser. No. 09/194,284 filed Jun. 10, 1999, now abandoned (U.S. National Phase application of PCT/IB97/00879), filed May 22, 1997, which is a continuation-in-part of U.S. Ser. No. 08/653,954, filed May 22, 1996 and now abandoned.

BACKGROUND OF THE INVENTION

1. Field of the Invention

The invention relates to modulation of gene expression. In particular, the invention relates to modulation of gene expression of the gene encoding DNA methyltransferase, and to modulation of gene expression that is regulated by the enzyme DNA methyltransferase.

2. Summary of the Related Art

Modulation of gene expression has become an increasingly important approach to understanding various cellular processes and their underlying biochemical pathways. Such understanding enriches scientific knowledge and helps lead to new discoveries of how aberrancies in such pathways can lead to serious disease states. Ultimately, such discoveries can lead to the development of effective therapeutic treatments for these diseases.

One type of cellular process that is of particular interest is how the cell regulates the expression of its genes. Aberrant gene expression appears to be responsible for a wide variety of inherited genetic disorders, and has also been implicated in numerous cancers and other diseases. Regulation of gene expression is a complex process, and many aspects of this process remain to be understood. One of the mysteries of this process resides in the fact that while the genetic information is the same in all tissues that constitute a multicellular organism, the expression of functions encoded by the genome varies significantly in different tissues.

In some cases, tissue-specific transcription factors are known to play a role in this phenomenon. (See Maniatis et al., Science 236: 1237–1245 (1987); Ingarham et al., Annual Review of Physiology 52: 773–791 (1990). However, several important cases exist that cannot be readily explained by the action of transcription factors alone. For example, Midgeon, Trends Genet. 10: 230–235 (1994), teaches that X-inactivation involves the inactivation of an allele of a gene that resides on the inactive X-chromosome, while the allele on the active X-chromosome continues to be expressed. In addition, Peterson and Sapienza, Annu. Rev. Genet. 27: 7–31 (1993), describes "parental imprinting", where an allele of a gene that is inherited from one parent is active and the other allele inherited from the other parent is inactive. In both of these cases, both alleles exist in an environment containing the same transcription factors, yet one allele is expressed and the other is silent. Thus, something other than transcription factors must be involved in these phenomena.

Investigators have been probing what type of "epigenetic information" may be involved in this additional control of the expression pattern of the genome. Holliday, Philos. Trans. R. Soc. Lond. B. Biol. Sci. 326: 329–338 (1990) discusses the possible role for DNA methylation in such epigenetic inheritance. DNA contains a set of modifications that is not encoded in the genetic sequence, but is added covalently to DNA using a different enzymatic machinery. These modifications take the form of methylation at the 5 position of cytosine bases in CG dinucleotides. Numerous studies have suggested that such methylation may well be involved in regulating gene expression, but its precise role has remained elusive. For example, Lock et al., Cell 48: 39–46 (1987), raises questions about whether the timing of hypermethylation and X-inactivation is consistent with a causal role for methylation. Similarly, Bartolomei et al., Genes Dev. 7: 1663–1673 (1993) and Brandeis et al., EMBO J. 12: 3669–3677 (1993), disclose timing/causation questions for the role of methylation in parental imprinting.

Some of the shortcomings of existing studies of the role of DNA methylation in gene expression reside in the tools that are currently available for conducting the studies. Many studies have employed 5-azaC to inhibit DNA methylation. However, 5-azaC is a nucleoside analog that has multiple effects on cellular mechanisms other than DNA methylation, thus making it difficult to interpret data obtained from these studies. Similarly, 5-azadC forms a mechanism based inhibitor upon integration into DNA, but it can cause trapping of DNA methyltransferase (MTase) molecules on the DNA, resulting in toxicities that may obscure data interpretation.

More recently, Szyf et al., J. Biol. Chem. 267: 12831–12836 (1995), discloses a more promising approach using expression of antisense RNA complementary to the DNA MTase gene to study the effect of methylation on cancer cells. Szyf and Von Hofe, PCT/US94/13685 (1994), discloses the use of antisense oligonucleotides complementary to the DNA MTase gene to inhibit tumorigenicity. These developments have provided powerful new tools for probing the role of methylation in numerous cellular processes. In addition, they have provided promising new approaches for developing therapeutic compounds that can modulate DNA methylation. One limitation to these approaches is that their effect is not immediate, due to the half life of DNA MTase enzyme. Thus, although the expression of DNA MTase is modulated, residual DNA MTase enzyme can continue to methylate DNA until such residual enzyme is degraded. There is, therefore, a need for new inhibitors of DNA MTase enzyme which are effective at inhibiting methylation, but without the toxic side effects of the earlier mechanism-based inhibitors.

BRIEF SUMMARY OF THE INVENTION

The invention provides novel inhibitors of DNA MTase enzyme and methods for using such inhibitors as analytical and diagnostic tools, as potentiators of transgenic plant and animal studies and gene therapy approaches, and as potential therapeutic agents.

In a first aspect, the invention provides novel hairpin oligonucleotide inhibitors of DNA methyltransferase (DNA MTase) enzyme. The normal substrate for DNA MTase is a hemimethylated double stranded DNA molecule having a CG dinucleotide opposite a 5-methyl CG dinucleotide, e.g., in a hairpin forming oligonucleotide. Methylation occurs at the 5-position of the cytosine base in the CG dinucleotide. The present inventors have discovered that substitution of the CG dinucleotide with a phosphorothioate IG, UG, 5-bromocytosineG, 5-fluorocytosineG, abasicG or CG dinucleotide in a hairpin forming oligonucleotide results in a powerful mechanism-based inhibitor of DNA MTase. Thus, inhibitors according to this aspect of the invention have the general structure:

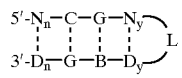

wherein each N is independently any nucleotide, n is a number from 0–20, C is 5-methylcytidine, G is guanidine, y is a number from 0–20, L is a linker, each D is a nucleotide that is complementary to an N such that Watson-Crick base pairing takes place between that D and the N such that the $N_n$-C-G-$N_y$ and the $D_n$-G-B-$D_y$ form a double helix, B is cytosine, inosine, uridine, 5-bromocytosine, abasic deoxyribose, or 5-fluorocytosine, dotted lines between nucleotides represent hydrogen bonding between the nucleotides, the linkage between G and B is a phosphorothioate or phosphorodithioate linkage and the total number of nucleotides ranges from about 10 to about 50. In one preferred embodiment, L is an oligonucleotide region having from 1 to about 10 nucleotides. DNA MTase inhibitors according to this aspect of the invention bind DNA MTase enzyme avidly in a noncovalent manner and inhibit DNA MTase in an S-adenosylmethionine (SAM)-independent manner.

In a second aspect, the invention provides inhibitors of DNA MTase enzyme which also inhibit the expression of the DNA MTase gene. Inhibitors according to this aspect of the invention have the general structure:

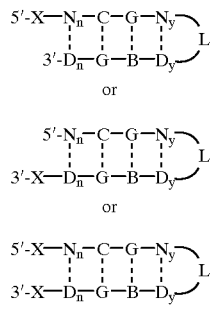

wherein the substituents are the same as for inhibitors according to the first aspect of the invention, except that X is an antisense oligonucleotide of from about 10 to about 50 nucleotides in length, which is complementary to a portion of an RNA encoding DNA MTase enzyme, and L can optionally be X.

In a third aspect, the invention provides a diagnostic method for determining whether a particular sample of cells is cancerous. The method according to this aspect of the invention comprises preparing an extract from the cells in the cell sample, adding labeled inhibitor according to the invention, measuring the extent of formation of a complex between the labeled inhibitor and DNA MTase enzyme, normalizing the level of such complex formation to the number of cells represented in the sample to obtain a normalized complex formation value, and comparing the normalized complex formation value to a normalized complex formation value for non-cancerous and/or cancerous cell samples. In a preferred embodiment, the extract is a nuclear extract. Because cancer cells express DNA MTase at much higher levels than do non-cancerous cells, the comparison of the normalized complex formation values is diagnostic for whether the cell sample is cancerous.

In a fourth aspect, the invention provides methods for inhibiting tumorigenesis comprising administering to an animal, including a human, inhibitors according to the invention. In the method according to this aspect of the invention a therapeutically effective amount of an inhibitor according to the invention is administered for a therapeutically effective period of time to an animal, including a human, which has cancer cells present in its body.

DETAILED DESCRIPTION OF THE PREFERRED EMBODIMENTS

Figure 1:
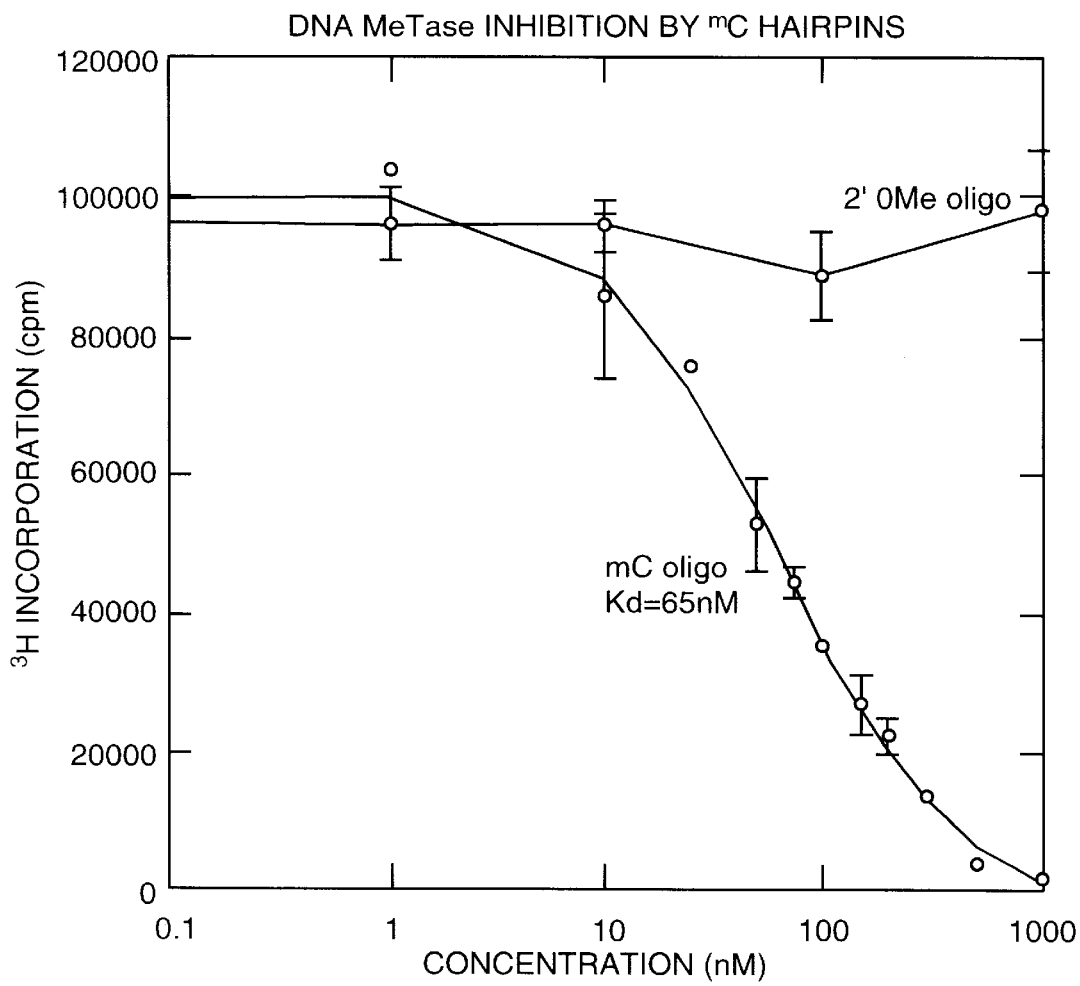
FIG. 1 is a diagrammatic representation showing inhibition of DNA MTase enzyme by certain preferred embodiments of DNA MTase enzyme inhibitors having the sequences of SEQ ID NO: 13 and SEQ ID NO: 4 according to the invention.
Figure 1:
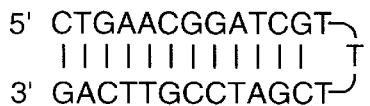
Figure 1:
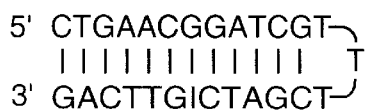

The invention relates to modulation of gene expression. In particular, the invention relates to modulation of gene expression of the gene encoding DNA methyltransferase, and to modulation of gene expression that is regulated by the enzyme DNA methyltransferase. The patents and publications identified in this specification are within the knowledge of those skilled in this field and are hereby incorporated by reference in their entirety.

The invention provides novel inhibitors of DNA MTase enzyme and methods for using such inhibitors as analytical and diagnostic tools, as potentiators of transgenic plant and animal studies and gene therapy approaches, and as potential therapeutic agents.

In a first aspect, the invention provides novel hairpin oligonucleotide inhibitors of DNA methyltransferase (DNA MTase) enzyme.

As used herein, "DNA methyltransferase" is a protein which is capable of methylating a particular DNA sequence.

In a preferred embodiment, the normal substrate for DNA MTase is a hemimethylated double stranded DNA molecule having a CG dinucleotide opposite a 5-methyl CG dinucleotide, e.g., in a hairpin forming oligonucleotide, and methylation occurs at the 5-position of the cytosine base in the CG dinucleotide. Most preferably, the DNA methyltransferase is mammalian DNA methyltransferase or M.SssI DNA methyltransferase.

The present inventors have discovered that substitution of the CG dinucleotide with a phosphorothioate IG, UG, 5-bromocytosineG, 5-fluorocytosineG, abasicG, or CG dinucleotide in a hairpin forming oligonucleotide results in a powerful mechanism-based inhibitor of DNA MTase. Thus, inhibitors according to this aspect of the invention have the general structure:

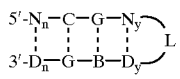

wherein each N is independently any nucleotide, n is a number from 0–20, C is 5-methylcytidine, G is guanidine, y is a number from 0–20, L is a linker, each D is a nucleotide that is complementary to an N such that Watson-Crick base pairing takes place between that D and the N such that the $N_n$-C-G-$N_y$ and the $D_n$-G-B-$D_y$ form a double helix, B is cytosine, inosine, uridine, 5-bromocytosine, abasic deoxyribose, or 5-fluorocytosine, dotted lines between nucleotides represent hydrogen bonding between the nucleotides, the linkage between G and B is a phosphorothioate or phosphorodithioate linkage and the total number of nucleotides ranges from about 10 to about 50. In one particularly preferred embodiment, L is a nucleoside or an oligonucleotide region having from 2 to about 10 nucleotides. Preferably, the indicated CG and GB and about 2 flanking nucleotides on either side are deoxyribonucleosides. DNA MTase inhibitors according to this aspect of the invention bind DNA MTase enzyme avidly in a noncovalent manner and inhibit DNA MTase in an S-adenosylmethionine (SAM)-independent manner.

Examples of certain preferred DNA MTase inhibitors according to this aspect of the invention include those having the following nucleotide sequences (hydrogen bonding not shown):

SEQ. ID. NO. 1
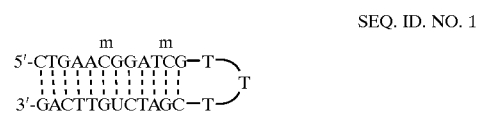

SEQ. ID. NO. 2
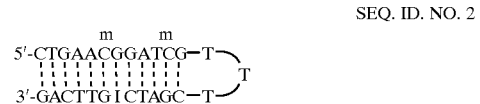

SEQ. ID. NO. 3
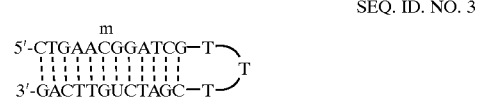

SEQ. ID. NO. 4
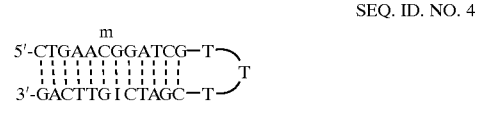

SEQ. ID. NO. 5
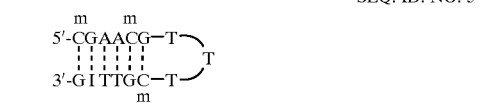

SEQ. ID. NO. 6

SEQ. ID. NO. 7

SEQ. ID. NO. 8
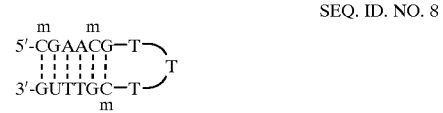

SEQ. ID. NO. 9

SEQ. ID. NO. 10

SEQ. ID. NO. 11

SEQ. ID. NO. 12
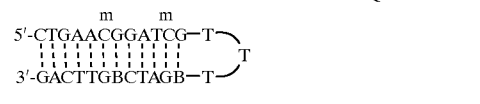

SEQ. ID. NO. 13
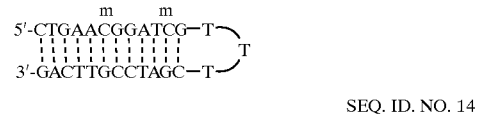

SEQ. ID. NO. 14
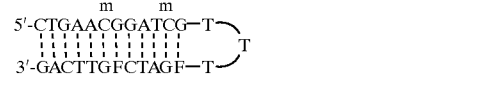

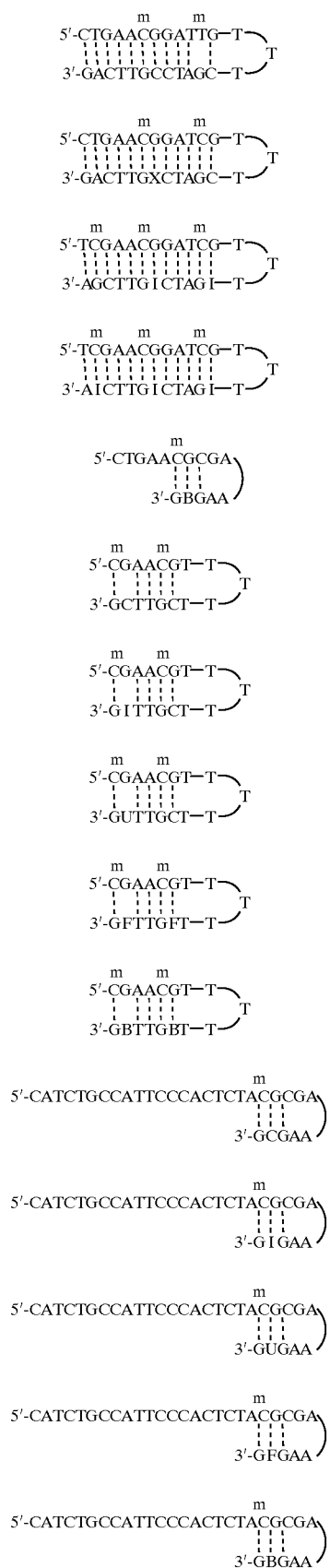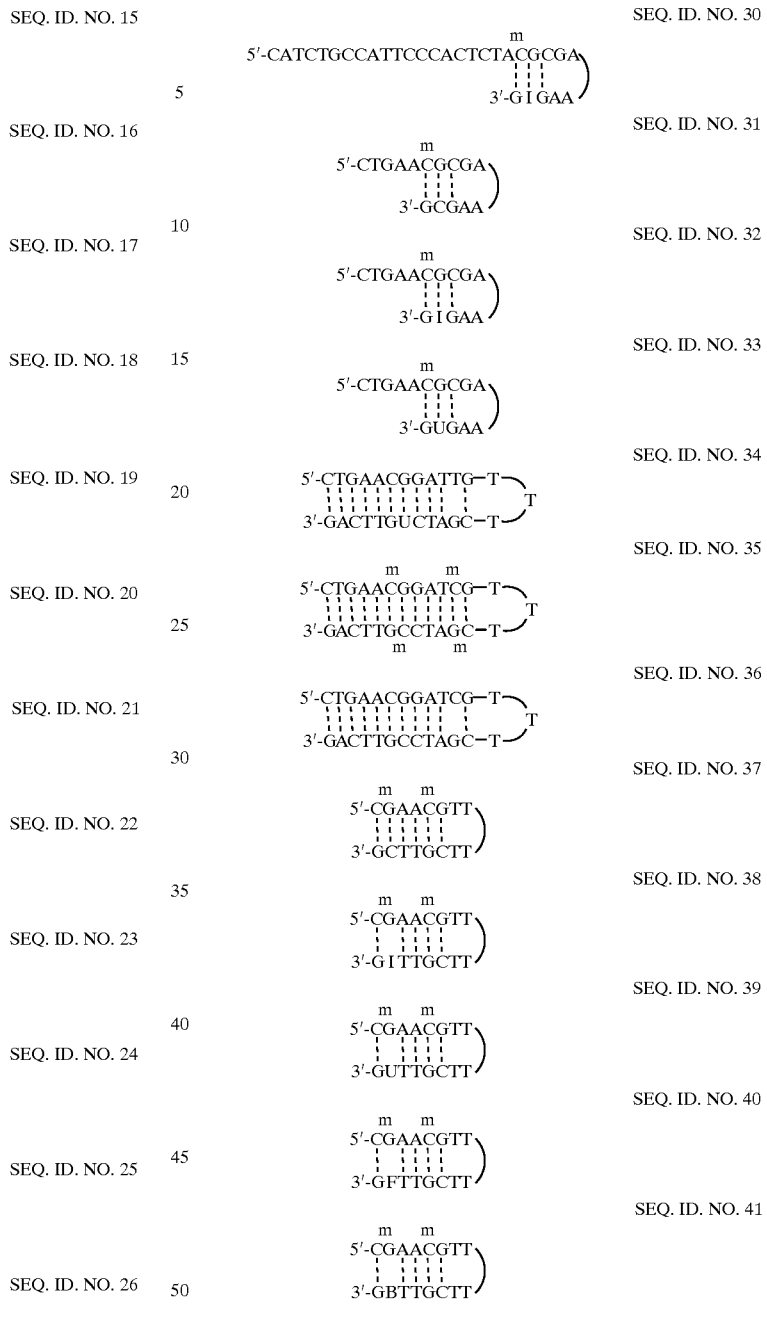

wherein C is cytidine, T is thymidine, A is adenosine, G is guanine, m is a methyl group at the 5-position of cytosine, B is cytosine, inosine, uridine, 5-bromocytidine, or 5-fluorouridine, X is any base and F is 5-fluorocytosine, and wherein the methyl acceptor site is a phosphorothioate or phosphorodithioate dinucleoside. As the methyl group is not actually transferred, "methyl acceptor site" means the dinucleoside which is substituted for the natural CG dinucleoside which would have been the methyl acceptor site.

From the foregoing, those skilled in the art will recognize that the overall sequence of the oligonucleotide inhibitor of DNA MTase is not critical, so long as it is capable of forming a hairpin oligonucleotide in which one strand has a 5-methylCG dinucleotide and the other strand has, opposite the 5-methylCG dinucleotide, an IG, UG, 5-bromocytosineG, abasicG, 5-fluorocytosineG or CG dinucleoside phosphorothioate or phosphorodithioate, preferably with both nucleosides being deoxyribonucleosides. In a preferred embodiment, seven or more consecutive nucleosides, including the methyl acceptor site, are phosphorothioate linked. Preferably, when two or more CG dinucleosides are present, they are spaced apart, rather than being in tandem. Where two or more CG dinucleosides are present, it is preferred that at least the CG dinucleoside furthest from the linker be a phosphorothioate or phosphorodithioate dinucleoside. In certain embodiments, two or more CG dinucleosides, or at least one CG and one TG nucleoside, are preferred. In such embodiments, the CG furthest from the linker is generally opposite the methyl acceptor site. It is preferred that at least one nucleoside on the strand which does not contain the methyl acceptor site be methylated, most preferably being a methylcytosine or a thymidine nucleoside. Where such nucleoside is opposite the G of the methyl acceptor site, methylcytosine is particularly preferred. Preferably the hairpin structure contains at least three base pairs, more preferably at least 6, and most preferably at least 12.

For purposes of the invention, the term "oligonucleotide" includes polymers of two or more deoxyribonucleotide, ribonucleotide, or 2'-O-substituted ribonucleotide monomers, or any combination thereof- Such monomers may be coupled to each other by any of the numerous known internucleoside linkages. In certain preferred embodiments, these internucleoside linkages may be phosphodiester, phosphotriester, phosphorothioate, or phosphoramidate linkages, or combinations thereof. In a particularly preferred embodiment the monomers are coupled by one or more phosphorothioate linkages.

The term oligonucleotide also encompasses such polymers having chemically modified bases or sugars and/ or having additional substituents, including without limitation lipophilic groups, intercalating agents, diamines and adamantane. For purposes of the invention the term "2'-O-substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

Inhibitors according to the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)).

DNA MTase inhibitors according to the invention are useful for a variety of purposes. For example, they can be used as "probes" of the physiological function of DNA MTase by being used to inhibit the activity of DNA MTase in an experimental cell culture or animal system and to evaluate the effect of inhibiting such DNA MTase activity. This is accomplished by administering to a cell or an animal a DNA MTase inhibitor according to the invention and observing any phenotypic effects. In this use, DNA MTase inhibitors according to the invention are preferable to traditional "gene knockout" approaches because they are easier to use and can be used to inhibit DNA MTase activity at selected stages of development or differentiation. Thus, DNA MTase inhibitors according to the invention can serve as probes to test the role of DNA methylation in various stages of development.

DNA MTase inhibitors according to the invention are useful as diagnostic probes for whether a cell sample is cancerous, as described in detail elsewhere in this specification. In addition, DNA MTase inhibitors according to the invention are useful for in vivo imaging of cancer cells. Since cancer cells have elevated levels of DNA MTase and normal cells do not, DNA MTase inhibitors according to the invention will form stable complexes with DNA MTase in cancer cells, but not in normal cells. Thus, appropriate labeling of DNA MTase inhibitors with an imaging agent, e.g., technecium, will result in localization of the label at the site of the cancer cells. This effect may be enhanced by using DNA MTase inhibitors which are unstable (e.g., oligonucleotide phosphodiesters) or rapidly cleared (e.g., oligonucleotide methylphosphonates) in the absence of complex formation, thus reducing background noise.

Finally, DNA MTase inhibitors according to the invention are useful in therapeutic approaches to cancer and other diseases involving suppression of gene expression. The anti-cancer utility of DNA MTase inhibitors according to the invention is described in detail elsewhere in this specification. In addition, DNA MTase inhibitors according to the invention may be used to activate silenced genes to provide a missing gene function and thus ameliorate disease symptoms. For example, the diseases beta thalassemia and sickle cell anemia are caused by aberrant expression of the adult beta globin gene. Most individuals suffering from these diseases have normal copies of the fetal gene for beta globin. However, the fetal gene is hypermethylated and is silent. Activation of the fetal globin gene could provide the needed globin function, thus ameliorating the disease symptoms.

For therapeutic use, DNA MTase inhibitors according to the invention may optionally be formulated with any of the well known pharmaceutically acceptable carriers or diluents. This formulation may further contain one or more additional DNA MTase inhibitors according to the invention. Alternatively, this formulation may contain one or more anti-DNA MTase antisense oligonucleotide or it may contain any other pharmacologically active agent.

In a second aspect, the invention provides inhibitors of DNA MTase enzyme which also inhibit the expression of the DNA MTase gene. Inhibitors according to this aspect of the invention have the general structure:

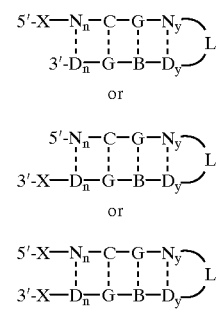

wherein the substituents are the same as for inhibitors according to the first aspect of the invention, except that X is an antisense oligonucleotide of from about 10 to about 50 nucleotides in length, which is complementary to a portion of an RNA encoding DNA MTase enzyme, and L can optionally be X. Particularly preferred embodiments have the antisense oligonucleotide coupled at one or both ends to one or more of the inhibitors selected from the group consisting of SEQ. ID. NOS. 1–41.

In a third aspect, the invention provides a diagnostic method for determining whether a particular sample of cells is cancerous. The method according to this aspect of the invention comprises preparing an extract from the cells in the cell sample, adding labelled inhibitor according to the invention, measuring the extent of formation of a complex between the labeled inhibitor and DNA MTase enzyme, normalizing the extent of such complex formation to the number of cells represented in the sample to obtain a normalized complex formation value, and comparing the normalized complex formation value to a normalized complex formation value for non-cancerous and/ or cancerous cell samples. In a preferred embodiment, the extract is a nuclear extract. Because cancer cells express DNA MTase at much higher levels than do non-cancerous cells, the comparison of the normalized complex formation values is diagnostic for whether the cell sample is cancerous.

In the diagnostic method according to this aspect of the invention, the extent of complex formation may be carried out in a variety of ways. For example, radiolabeled inhibitor may be used and the extent of incorporation of the inhibitor into a complex of appropriate size (e.g., 190 kDa for a 27-mer inhibitor) can be determined. Alternatively, anti-DNA MTase antisera can be employed to determine the quantity of complex of appropriate size which is present. In another embodiment, antibodies or other binding partners can be prepared which recognize only the complex formed between the inhibitor and DNA MTase, and thus can be used to measure it formation. Normalizing the extent of complex formation to the number of cells can similarly be carried out in a variety of ways. For example, the number of cells in the test sample, as well as in the non-cancerous and cancerous control samples, can be counted prior to extract formation. Alternatively, the total amount of protein in each of the extracts can be determined using standard procedures. The normalized complex formation value can then be determined by dividing the extent of complex formation by the number of cells in the sample or the amount of protein in the extract.

In a fourth aspect, the invention provides methods for is inhibiting tumorigenesis comprising administering to an animal, including a human, inhibitors according to the invention. In the method according to this aspect of the invention a therapeutically effective amount of a DNA MTase inhibitor according to the invention is administered for a therapeutically effective period of time to an animal, including a human, which has cancer cells present in its body. Preferably, such administration should be parenteral, oral, sublingual, transdermal, topical, intranasal or intrarectal. Administration of the therapeutic compositions can be carried out using known procedures at dosages and for periods of time effective to reduce symptoms or surrogate markers of the cancer. When administered systemically, the therapeutic composition is preferably administered at a sufficient dosage to attain a blood level of DNA MTase inhibitor from about 0.01 micromolar to about 10 micromolar. For localized administration, much lower concentrations than this may be effective, and much higher concentrations may be tolerated. Preferably, a total dosage of DNA methyltransferase inhibitor will range from about 0.1 mg oligonucleotide per patient per day to about 200 mg oligonucleotide per kg body weight per day. It may desirable to administer simultaneously, or sequentially a therapeutically effective amount of one or more of the therapeutic compositions of the invention to an individual as a single treatment episode.

The following examples are intended to further illustrate certain preferred embodiments of the invention and are not limiting in nature.

EXAMPLE 1

Inhibition of DNA MTase Activity in Nuclear Extracts Prepared from Human or Murine Cells Nuclear extracts were prepared from $1 \times 10^9$ mid-log phase human H446 cells, human A549 cells or mouse Y1 cells. The cells were harvested and washed twice with phosphate buffered saline (PBS), then the cell pellet was resuspended in 0.5 ml Buffer A (10 mM Tris pH 8.0, 1.5 mM $MgCl_2$, 5 mM $KCl_2$, 0.5 mM DTT, 0.5 mM PMSF and 0.5% Nonidet P40) to separate the nuclei from other cell components. The nuclei were pelleted by centrifugation in an eppendorf microfuge at 2,000 rpm for 15 min at 4° C. The nuclei were washed once in Buffer A and repelletted, then resuspended in 0.5 ml Buffer B (20 mM Tris pH 8.0, 0.25% glycerol, 1.5 mM $MgCl_2$, 0.5 mM PMSF, 0.2 mM EDTA 0.5 mM DTT and 0.4 mM NaCl). The resuspended nuclei were incubated on ice for 15 minutes then spun at 15,000 rpm to pellet nuclear debris. The nuclear extract in the supernatant was separated from the pellet and used for assays for DNA MTase activity. For each assay, carried out in triplicate, 3 micrograms of nuclear extract was used in a reaction mixture containing 0.1 micrograms of a synthetic 33-base pair hemimethylated DNA molecule substrate with 0.5 $\mu$Ci S-[methyl-$^3$H] adenosyl- L-methionine (78.9 Ci/mmol) as the methyl donor in a buffer containing 20 mM Tris HCl (pH 7.4), 10 mM EDTA, 25% glycerol, 0.2 mM PMSF, and 20 mM 2-mercaptoethanol. The reaction mixture was incubated for 1 hour at 37° C. to measure the initial rate of the DNA MTase. The reaction was stopped by adding 10% TCA to precipitate the DNA, then the samples were incubated at 4° C. for 1 hour and the TCA precipitates were washed through GFC filters (Fischer). Controls were DNA incubated in the reaction mixture in the absence of nuclear extract, and nuclear extract incubated in the reaction mixture in the absence of DNA. The filters were laid in scintillation vials containing 5 ml scintillation cocktail and tritiated methyl groups incorporated into the DNA were counted in a beta scintillation counter. To measure inhibition of DNA MTase activity by different inhibitors, parallel reactions were carried out in which the inhibitors were added to the reaction mixtures in increasing concentrations ranging from 1 to 1000 nM. The control inhibitors had the same nucleotide sequence as the test inhibitors, except that the control inhibitor had an o-methyl modified ribose, or was a scrambled oligonucleotide, whereas the test inhibitors had either an IG or UG dinucleotide, or a $^{5\text{-}}$ bromocytosine G, or a 5-fluorocytosine G dinucleotide or a cytosine opposite the 5-methylCG dinucleotide. The $EC_{50}$ was calculated as the concentration of inhibitor required to inhibit 50% of the DNA MTase activity present in the nuclear extract.

Test inhibitors showed an $EC_{50}$ of less than 1 $\mu$M with some emibodiments showing an $EC_{50}$ of as low as 30 nM. See FIG. 1. The control inhibitor could not produce an $EC_{50}$ at any concentration tested (up to 1 $\mu$M). Representative data using the test inhibitors of the invention are shown in table 1.

TABLE 1

| EC$_{50}$ | SEQ. ID. NO. |
|---|---|
| 30 nM | 1 |
| 30 nM | 2 |
| 350 nM | 4 |
| 30 nM | 13 |
| 50 nM | 14 |
| 50 nM | 15 |
| 350 nM | 16 |
| 350 nM | 17 |
| 450 nM | 18 |
| 450 nM | 19 |
| 500 nM | 20 |
| 500 nM | 21 |
| 500 nM | 22 |
| 230 nM | 23 |
| 230 nM | 24 |
| 300 nM | 25 |
| 300 nM | 26 |
| 300 nM | 27 |
| 300 nM | 28 |
| 50 nM | 29 |
| 500 nM | 30 |
| 700 nM | 31 |
| 600 nM | 32 |
| 600 nM | 33 |
| 650 nM | 34 |
| 35 nM | 35 |
| 400 nM | 36 |
| 500 nM | 37 |
| 500 nM | 38 |
| 500 nM | 39 |
| 230 nM | 40 |
| 230 nM | 41 |

These results demonstrate that substitution of an IG or UG or CG dinucleotide, or a 5-bromocytosine G, or a 5-fluorocytosine G dinucleotide opposite a 5-methylCG dinucleotide in a synthetic hairpin forming oligonucleotide results in an effective inhibitor of DNA MTase activity.

Figure 9:
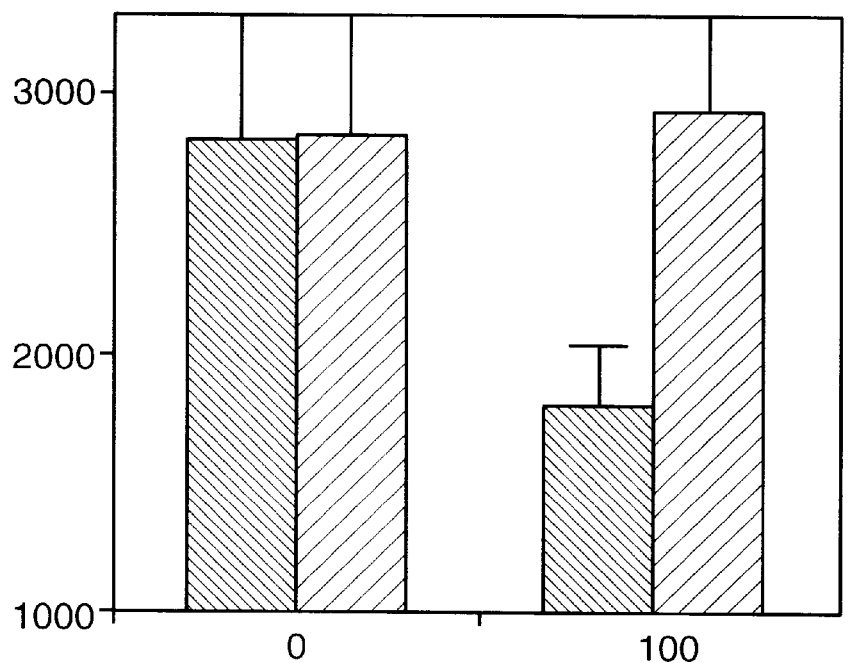
FIG. 9 is a diagrammatic representation showing inhibition of DNA MTase activity in cells treated with the hemimethylated test inhibitor having the sequence of SEQ. ID. NO. 13 at a concentration of 100 nM.

The results shown in FIG. 9 demonstrate that the hemi-methylated test inhibitor having the sequence of SEQ. ID. NO. 13 at a concentration of 100 nM inhibited DNA MTase activity as compared to the control nonmethylated hairpin.

EXAMPLE 2

Complex Formation Between DNA MTase Inhibitors and DNA MTase Enzyme

To measure the rate of complex formation between different DNA MTase inhibitors and DNA MTase enzyme, different inhibitors (each at 4 micromolar concentration) were labeled using polynucleotide kinase and gamma $^{32}$P-ATP (300 mCi/mmol, 50 μCi) (New England Biolabs, Beverly, Mass.) as recommended by the manufacturer. Labeled oligonucleotide was separated from nonincorporated radioactivity by passing through a G-50 Sephadex spin column (Pharmacia, Uppsala, Sweden). Labeled inhibitors (500 nM) were incubated with 5 micrograms nuclear extract prepared as described in Example 1. The incubation, in the same buffer used for the DNA MTase activity assay, was at 37° C. for 30 minutes. To determine whether complex formation was dependent on the cofactor SAM, the reaction was carried out both in the presence and the absence of SAM). Then, loading dye (0.3 M Tris-HCl pH 8.8, 0.2% SDS, 10% glycerol, 28 mM 2-mercaptoethanol and 24 μg/ml bromophenol blue) was added and the sample was separated on a 5% SDS-polyacrylamide gel (SDS-PAGE) with a 4% stacking gel according to standard procedures. Following SDS-PAGE separation, the gel was exposed to autoradiography for visualization of a complex migrating at 190 kDa. Alternatively, the gel was electrotransferred onto a PVDF membrane (Amersham Life Sciences, Buckinghamshire, England) using a BioRad (Hercules, Calif.) electrotransfer apparatus at 250 milliamperes for 2.5 hours in electrotransfer buffer (3.03 g/l Tris base, 14.4 g/l glycine, 1 g/l SDS, pH 8.3) for Western blotting with a DNA MTase-specific antisera. The membrane was blocked for 1 hour in a buffer containing 5 mM Tris base, 200 mM NaCl, 0.5% Tween-20 and 5% dry milk. Rabbit antisera was raised according to standard procedures against a peptide sequence found in the catalytic domain of human and murine DNA MTase. The antisera was added to the membrane at a 1:200 dilution and incubated for 1 hour. The membrane was washed with the blocking buffer, then reacted with a 1:5000 dilution of goat anti-rabbit secondary antibody (Amersham) for an additional hour. The membrane was then washed for 10 minutes in blocking buffer, three times, and bands reacting with anti-DNA MTase antibody were visualized using an ECL detection kit (Amersham).

Figures 2A, 2B, 2C, 2D:
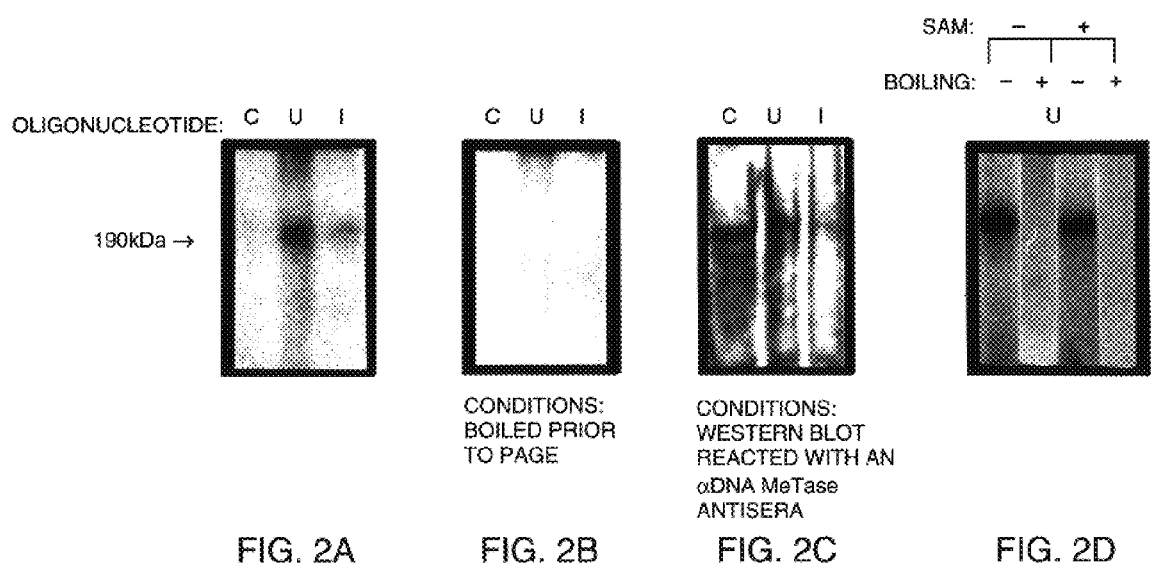
FIGS. 2A–2D are representations of autoradiographs (panels A, B and D) and Western blots (panel C) in an experiment to identify complex formation between DNA MTase inhibitors and DNA MTase enzyme. Complex formation was reversed by boiling, and was independent of SAM.
Figure 3:
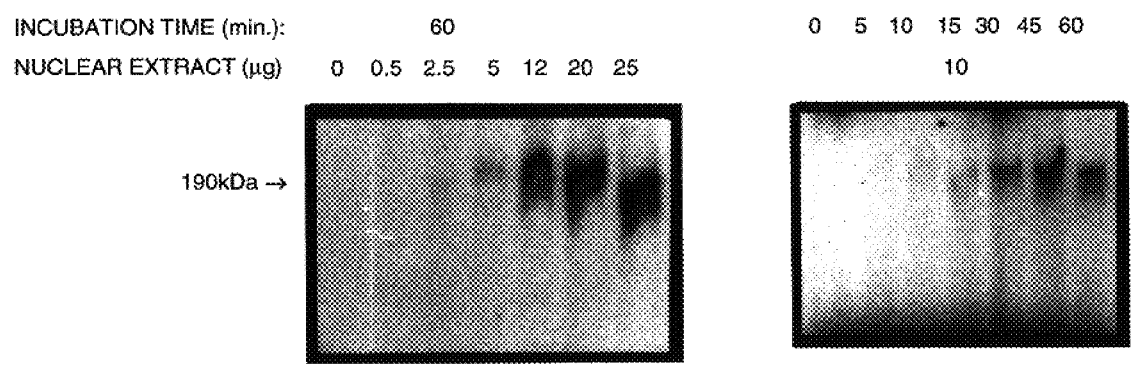
FIG. 3 are representations of Western blots showing that the complex formation between DNA MTase inhibitors and DNA MTase enzyme is completed within 30 minutes.

Typical results are shown in FIGS. 2 and 3. The results shown in FIG. 2 demonstrate that a 190 kDa complex is detected by both autoradiography and Western blotting, strongly indicating that the 190 kDa complex is formed between the DNA MTase inhibitors and DNA MTase enzyme. These results further demonstrate that such complex formation is independent of the cofactor SAM. The results shown in FIG. 3 demonstrate that the complex formation is complete within 30 minutes, thus suggesting that such complex formation provides an assay for the level of DNA MTase in different cell samples.

Figure 13:
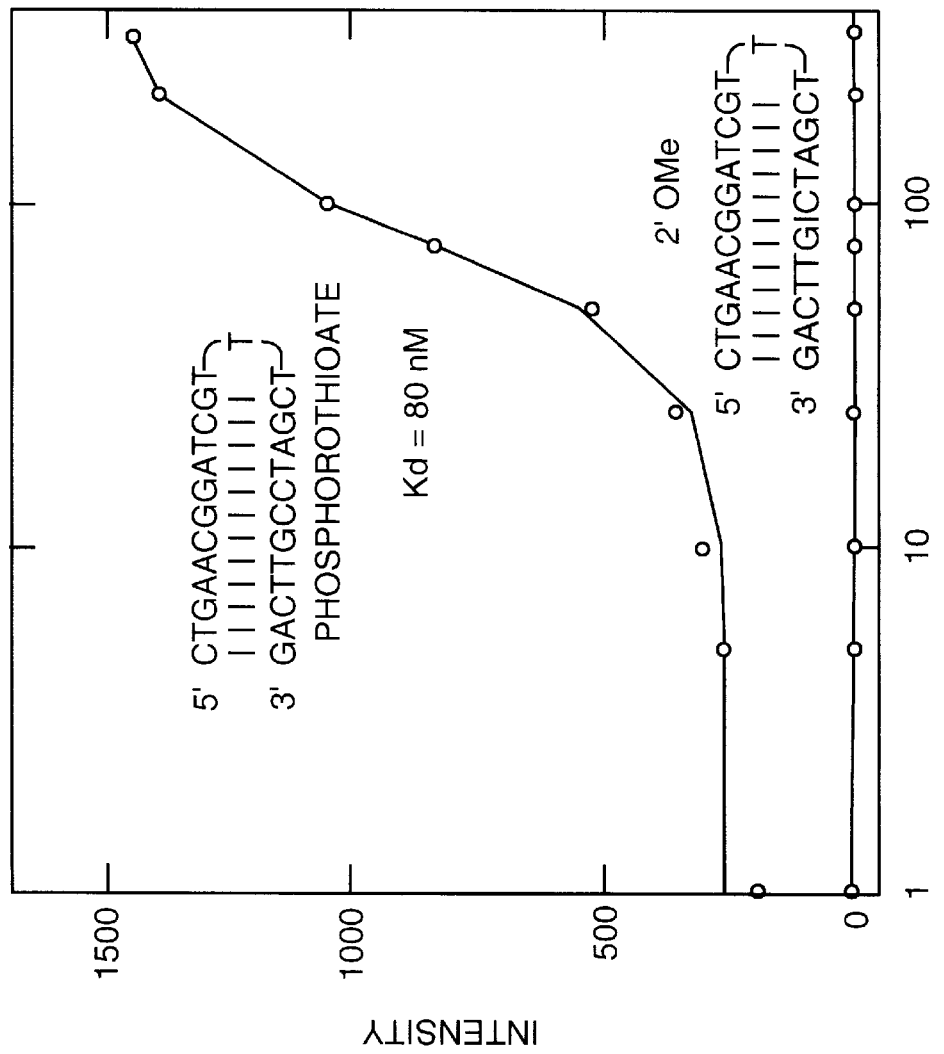
FIG. 13 is a diagrammatic representation of a gel shift assay showing the binding of human DNA MTase to the MTase enzyme inhibitors (SEQ ID NO: 13 and SEQ ID NO: 4) according to the present invention.

In addition, nuclear extracts prepared as described in Example 1, were incubated with labeled inhibitors to perform gel shift assays according to standard protocols (see e.g., Molecular Cloning, 2d Edition, Cold Spring Harbor Laboratory Press (1989)). The results shown in FIG. 13, further demonstrate the binding of human DNA methyltransferase to the inhibitors of the invention.

EXAMPLE 3

Figure 4A:
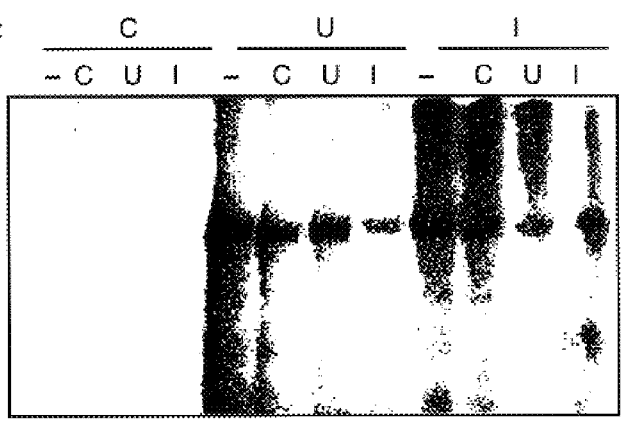
FIG. 4 are representations of Western blots, panel A shows results of complex formation studies in which nuclear extracts were incubated with labeled oligonucleotide substrate (C) or inhibitor (I or U), followed by addition of a 100-fold excess of unlabeled substrate or inhibitor. Panel B shows results of complex formation studies in which nuclear extracts were incubated with 50 μM unlabeled oligonucleotide substrate (C), inhibitor (I or U), or with natural hemimethylated DNA substrate (HM) followed by addition of 0.5 μM labeled substrate or inhibitor.
Figure 4B:
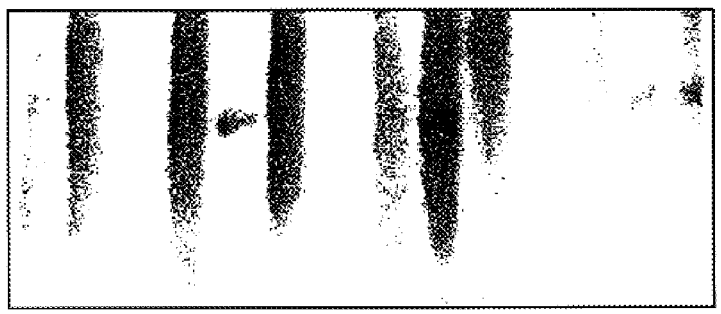

Stability of Noncovalent ComDlex Formation Between DNA MTase Inhibitors and DNA MTase Enzyme To determine the stability of the complex between DNA MTase inhibitors and DNA MTase enzyme, relative to the stability of the complex between normal substrate and DNA MTase enzyme, binding competition assays were carried out as follows. Complex formation was carried out as described in Example 2, except that the labeled substrate or inhibitor was allowed to form a complex with the DNA MTase, followed by addition of a 100-fold excess of unlabeled substrate or inhibitor. The substrate was a hairpin is forming oligonucleotide having a 5-methylCG dinucleotide on one strand, opposite a CG dinucleotide on the other strand. The inhibitors were identical, except that they had an IG or UG dinucleotide on the other strand. The results are shown in FIG. 4, panel A. Where complex formation was originally carried out using the substrate oligonucleotide, no radiolabeled complex was detected, suggesting that the complex is labile. However, where complex formation was originally carried out using either the IG or the UG inhibitor, the excess unlabeled substrate or inhibitor was unable to displace the radiolabel from the complex, indicating that the DNA MTase inhibitor-DNA MTase enzyme complex is very stable, with a slow off rate.

Alternatively, when 50 μM unlabeled substrate or inhibitor was pre-incubated with the nuclear extract, subsequent incubation with 0.5 µM radiolabeled substrate or inhibitor could not displace the unlabeled substrate or inhibitor from the complex. However, the labeled inhibitor could displace unlabeled hemi-methylated DNA, the natural substrate for DNA MTase, from such a pre-formed complex. These results demonstrate that binding of the inhibitors to DNA MTase enzyme is specific and saturable, and that such inhibitors are efficacious competitors of the natural substrate of DNA MTase (FIG. 4, panel B).

EXAMPLE 4

Figure 5:
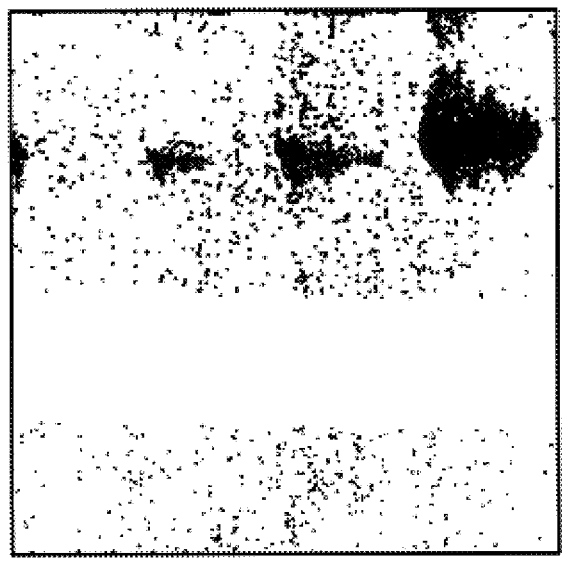
FIG. 5 is a representation of a blot showing time-dependent cellular uptake of a preferred embodiment of DNA MTase enzyme inhibitors according to the invention.

DNA MTase Inhibitor Accumulation and Formation of Complexes with DNA MTase Enzyme in Cells DNA MTase inhibitors were labeled with $^{32}$P as described in Example 2. 300,000 Y1 cells were plated per well in a six well tissue culture plate. Labeled inhibitors were added to a final concentration of 1 micromolar. Cells were harvested at different time points by trypsinization and washed extensively with PBS to remove nonincorporated compounds. The cell pellet was resuspended in 20 µl buffer RIPA (0.5% deoxycholic acid, 0.1% SDS, 1% NP-40, in PBS). The homogenate was incubated at 4° C. for 30 minutes, then spun in a microfuge at maximum speed for 30 minutes, after which the supernatant was transferred to a new tube. Two pl of supernatant were extracted with phenol-chloroform and loaded onto a 20% polyacrylamide-urea gel. Visualization was by autoradiography. The results demonstrated that the DNA MTase inhibitors were taken up by the cells in a time-dependent manner (FIG. 5). Ten microliters of the supernatant are loaded directly on 5% SDS-PAGE and visualized by autoradiography to detect complex formation. It is expected that the 190 kDa complex between the 27-mer DNA MTase inhibitor and DNA MTase enzyme will be observed.

EXAMPLE 5

Figure 8:
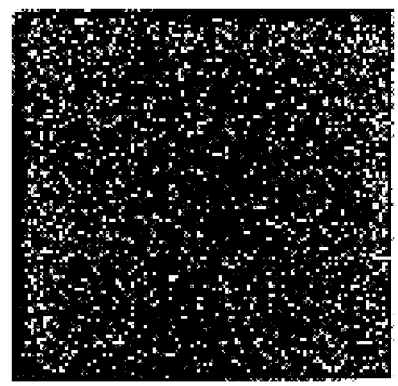
FIG. 8 are representations of blots showing the intracellular localization in the nucleus of hemimethylated-hairpin substrate of DNA Mtase 1 hour post treatment (Panel A), 4 hours post treatment (Panel B), and 24 hours post treatment (Panel C).
Figure 8:
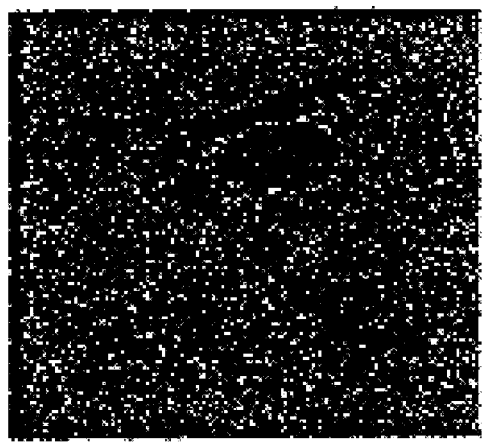
Figure 8:
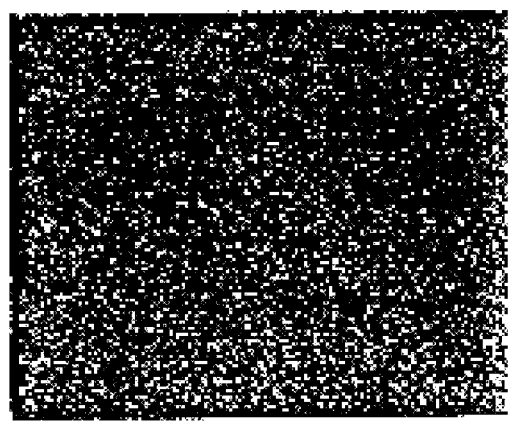

Intracellular Localization of DNA MTase Inhibitors 100 nM of oligonucleotide having the sequence shown as SEQ. ID. NO. 22 were labeled with the mixed isomeric N-hydroxysuccinimide esters of 5(6)-carboxyfluorescein (Molecular Probes, Eugene, Oreg.) as described by Sinha and Striepeke in Oligonucleotides and Analogues: A Practical Approach (1991)(Eckstein, Ed.) Oxford University Press, NY) pp 185–210. In a typical reaction, 28 nmol of oligonucleotide was dissolved in 180 1 of 0.4 M NaHCO$_3$/ Na$_2$CO$_3$ pH 9.0, 1 M N-dimethylformamide/water (3:2:1 v/v/v). This solution was diluted with an equal volume of water, and 1.5 mg of active ester of the fluorophore was added. The mixture was kept at room temperature in the dark for 17 h with gentle shaking and then diluted to 6 ml with water. Most of the excess dye was removed by extraction of the aqueous solution with n- butanol followed by ethanol precipitation according to standard methods. Human lung carcinoma A549 cells were grown to 10-5 and incubated with the labeled inhibitor in the presence of 10ug/me i,; lipofectin. The subcellular localization of the labeled inhibitor at different time points was determined by fluorescent microscopy. As shown in FIG. 8, a diffuse pattern of distribution of the test inhibitor in the cytosol and in the nuclei was observed 1 hour post treatment. At 4 hours post treatment almost all the test inhibitor was localized in the nucleus the site of action of DNA MTase. At 24 hours, the test inhibitor was mainly in the nucleus distributed in a punctate manner which is similar to the pattern of localization of DNA MTase. This experiment demonstrates that the DNA inhibitor is localized in the site of action of DNA MTase.

EXAMPLE 6

Analysis of Cellular DNA Methylation in Cells Treated with DNA MTase Inhibitors Nuclear extracts were prepared from untreated cells and from DNA MTase inhibitor-treated cells (1 µM inhibitor having SEQ ID NO: 13) according to the methodology described in Example 1. The DNA pellet was resuspended in 0.5 ml DNA extraction buffer (0.15 M NaCl, 1% SDS, 20 mM Tris-HCl pH 8.0, 5 mM EDTA), then 100 µg protease K was added and the suspension was incubated at 50° C. for 16 hours. The DNA was extracted in phenol-chloroform by adding 0.25 ml phenol and 0.25 ml chloroform. The suspension was mixed and the organic and aqueous phases were separated by centrifugation in a microfuge for 10 minutes at 15,000 rpm. One ml absolute ethanol was added to the aqueous phase and the DNA was precipitated by centrifugation in a microfuge for 15 minutes at 15,000 rpm. The DNA pellet was washed in 70% ethanol and repelleted by centrifugation. The DNA was resuspended in 100 µl 20 mM Tris-HCl pH 8.0, 1 mM EDTA.

Figure 10:
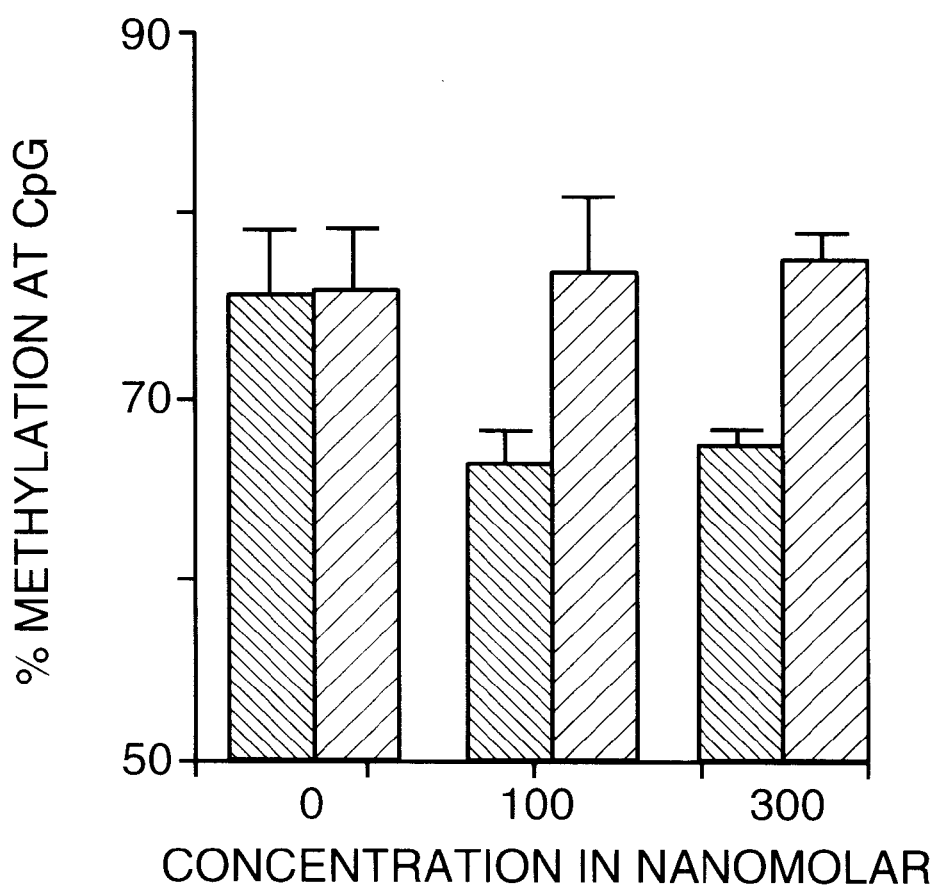
FIG. 10 is a diagrammatic representation showing an overall reduction in the percentage of non-methylated CG dinucleotides in DNA MTase inhibitor-treated cells as compared to untreated cells.

Two µg DNA were incubated at 37° C. for 15 minutes with 0.1 unit of DNAase, 2.5 µl $^{32}$P-alpha-dGTP (3000 Ci/mmol, Amersham) and then 2 units Kornberg DNA polymerase (Boehringer Mannheim, Mannheim, Germany) were added and the reaction mixture was incubated for an additional 25 minutes at 30° C. Fifty µl water was then added and nonincorporated radioactivity was removed by spinning through a Microspin S-300 HR column (Pharmacia). Labelled DNA(20 µl) was digested with 70 µg micrococcal nuclease (Pharmacia) in the manufacturer's recommended buffer for 10 hours at 37° C. Equal amounts of radioactivity were loaded onto TLC phosphocellulose plates (Merck, Darmstadt, Germany) and the 3' mononucleotides were separated by chromatography in one direction, in 66:33:1 isobutyric acid/H$_2$O/NH$_4$OH. The chromatograms were exposed to XAR film (Eastman Kodak, Rochester, N.Y.) and the autoradiograms were scanned by laser densitometry (Scanalytics, CSPI, Billerica, Mass.). Spots corresponding to cytosine and 5-methylcytosine were quantified and the percentage of non-methylated CG dinucleotides was determined. The results shown in FIG. 10 demonstrate an overall reduction in the percentage of non-methylated CG dinucleotides in DNA MTase inhibitor-treated cells, relative to untreated cells.

To asses demethylation of specific genes, a procedure is carried out as generally described in J. Biol. Chem. 270: 12690–12696 (1995). Briefly, the genomic DNA (10 µg) is extracted and subjected to digestion by 25 units HindIII, followed by digestion by either 25 units MspI (CG methylation insensitive) or 25 units HpaII (CG methylation sensitive) for 8 hours at 37° C. The digested DNA is separated on a 1.5% agarose gel and subjected to Southern blotting and hybridization with specific probes. The results are expected to show that genes which are ordinarily heavily methylated in the test cells become undermethylated, whereas the methylation levels for genes which are not ordinarily heavily methylated in the test cells are not significantly affected.

EXAMPLE 7

Inhibition of Tumorigenesis By Inhibitors of DNA MTase

Figure 6:
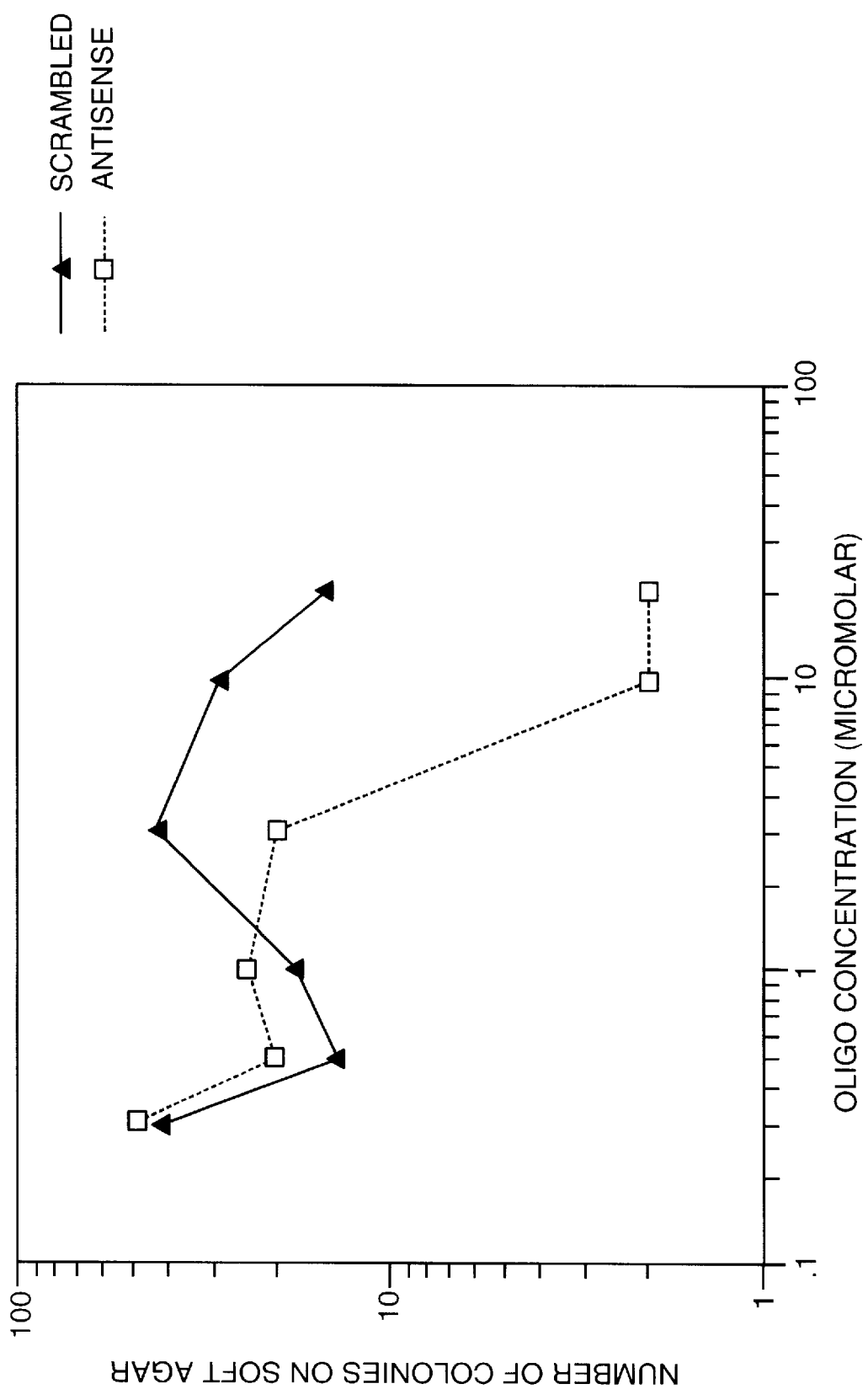
FIG. 6 is a diagrammatic representation showing dose-dependent inhibition of soft agar colony formation by Y1 cells treated with antisense oligonucleotides complementary to DNA MTase coding sequence.
Figure 11:
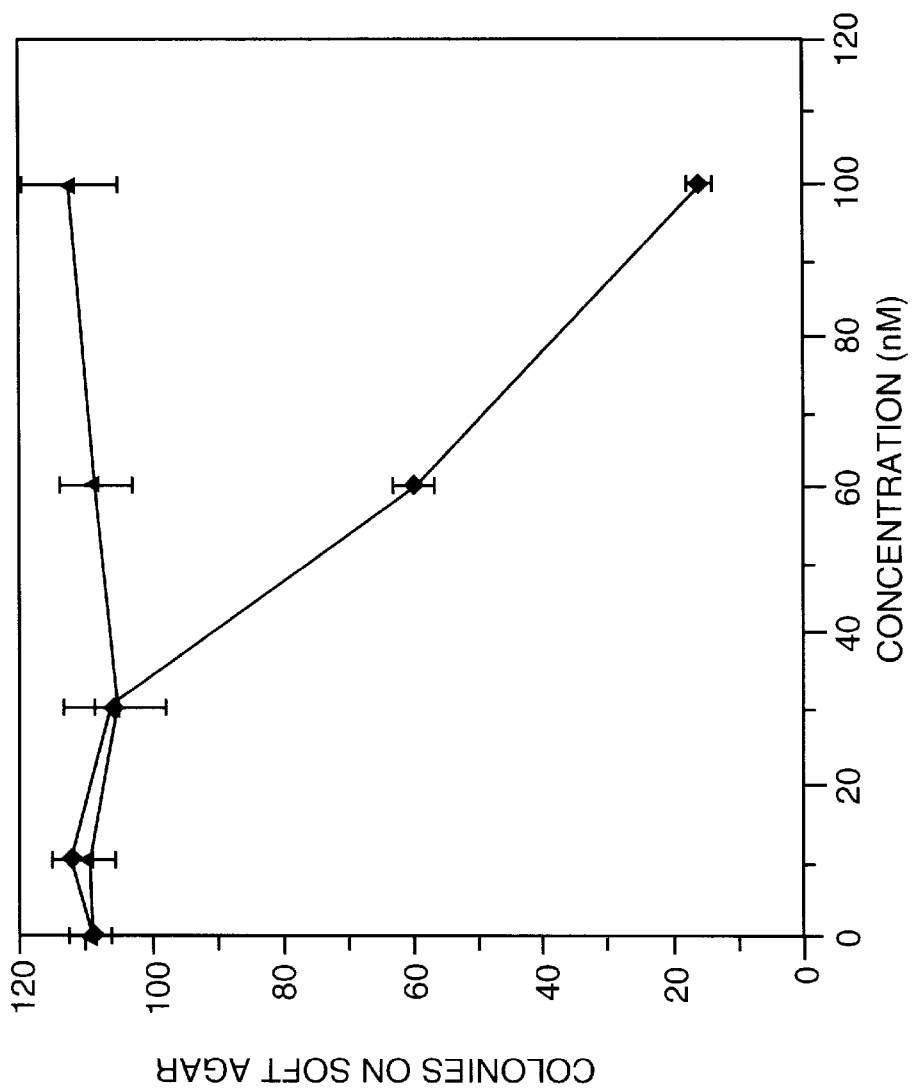
FIG. 11 is a diagrammatic representation showing a dose-dependent reduction in growth on soft agar observed following treatment with DNA MTase enzyme inhibitors according to the invention.
Figure 12:
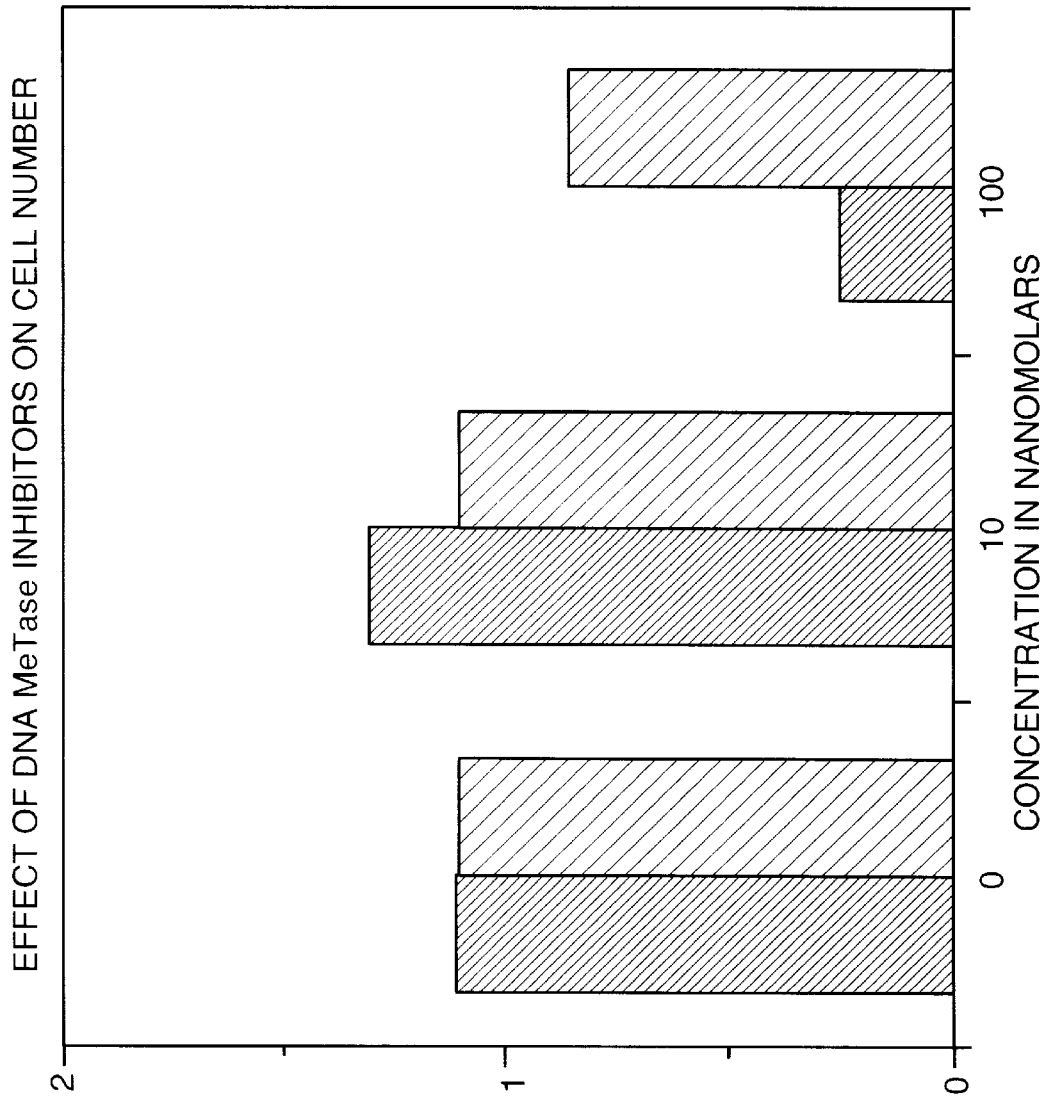
FIG. 12 is a diagrammatic representation showing a dose-dependent reduction in cell number following treatment with DNA MTase enzyme inhibitors according to the invention.

A549 cells were plated on a 6 well plate at a density of 80,000 cells/well. DNA MTase enzyme inhibitors (from about 10 to about 1000 nanomolar) or antisense oligonucleotide phosphorothioates complementary to the DNA MTase coding sequence (about 0.5 to 20 micromolar) were added to the cells. The cells were similarly treated daily for 3 days. Then, the cells were harvested and 3,000 live cells were plated in soft agar, as described in Freedman and Shin, Cell 3: 355–359 (1974). Two weeks after plating, the number of colonies formed in soft agar were scored by visual examination. In the case of antisense oligonucleotides, a dose-dependent reduction in the number of colonies was observed (FIG. 6). The results shown in FIG. 11 demonstrate a dose-dependent reduction in growth on soft agar observed following 3 days treatment with DNA MTase enzyme inhibitors. The results shown in FIG. 12 demonstrate a dose-dependent reduction cell number treatment with DNA MTase enzyme inhibitors.

Figure 7B:
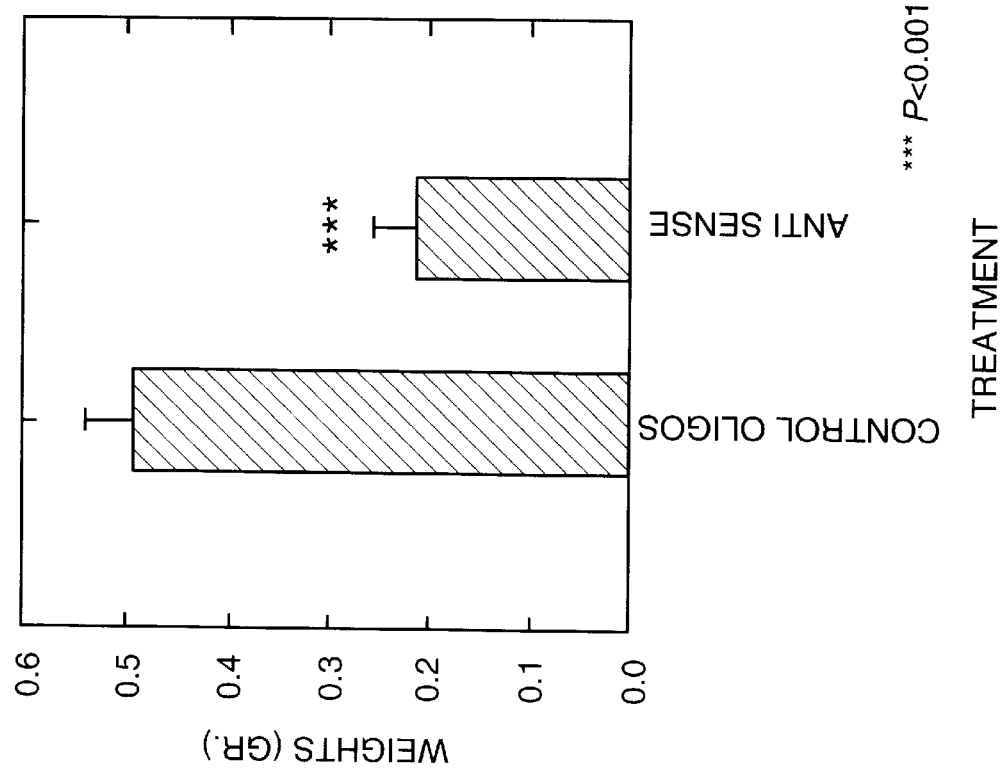
FIGS. 7A–7B are diagrammatic representations showing reduction in tumor size in tumor bearing mice treated with antisense oligonucleotides complementary to DNA MTase coding sequence.
Figure 7A:
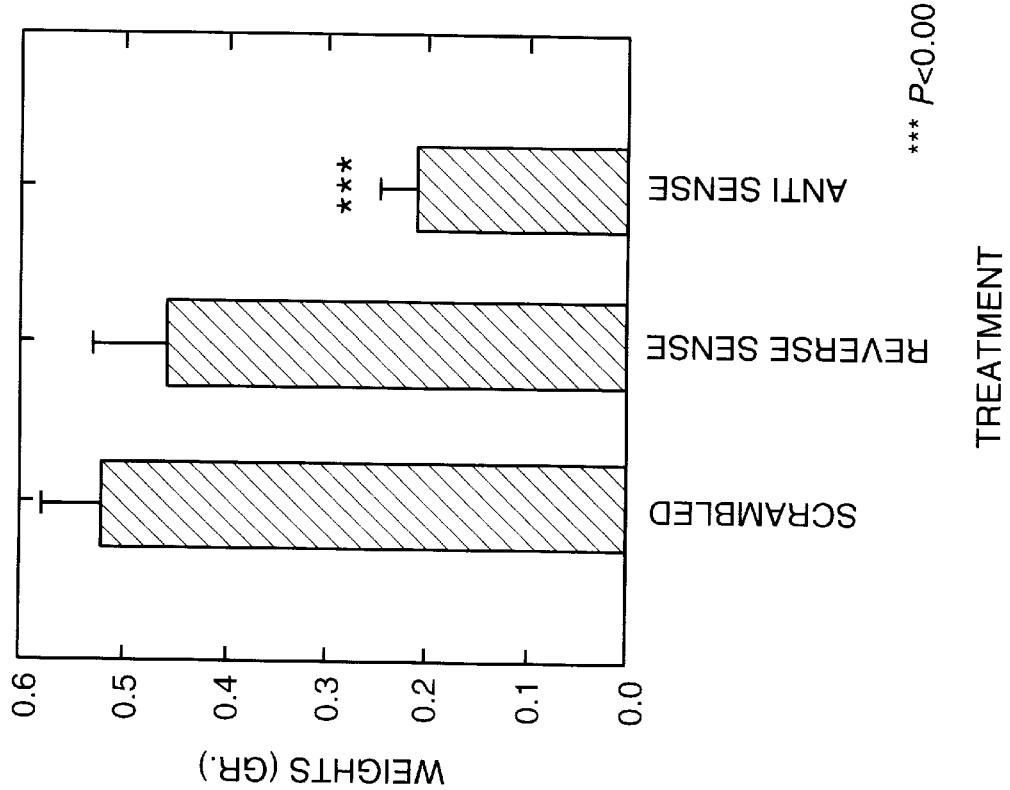

Alternatively, 6 to 8 week old LAF-1 mice (Jackson Labs, Bar Harbor, Me.) are injected subcutaneously in the flank area with $2 \times 10^6$ Y1 cells. Three days later, the mice are injected with 1–5 mg/kg antisense oligonucleotide phosphorothioates complementary to DNA MTase coding sequence, or with 5 mg/kg DNA MTase enzyme inhibitor. This dosing is repeated every two days. After one month, the mice are sacrificed and the tumor size is determined. In the case of the antisense oligonucleotides, significant reduction in tumor size was observed, relative to controls treated with a randomized or a reverse antisense sequence (FIG. 7). Similar results are expected for the DNA MTase enzyme inhibitors.

What is claimed is:

1. An inhibitor of DNA methytransferase enzyme having the general structure:

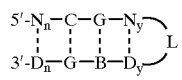

wherein each N is independently any nucleotide, n is a number from 0–20, C is 5-methylcytidine, G is guanidine, y is a number from 0–20, L is a linker, each D is a nucleotide that is complementary to an N such that Watson-Crick base pairing takes place between that D and the N such that the $N_n$-C-G-$N_y$ and the $D_n$-G-B-$D_y$ form a double helix, B is cytosine, inosine, uridine, 5-bromocytosine or 5-fluorocytosine, or abasic deoxyribose, the linkage between B and G is a phosphorothioate or phosphorodithioate linkage, dotted lines between nucleotides represent hydrogen bonding between the nucleotides, and the total number of nucleotides ranges from about 10 to about 50.

2. The inhibitor of DNA methytransferase enzyme according to claim 1, wherein the inhibitor is labeled.

3. The inhibitor of DNA methytransferase enzyme according to claim 1, wherein L is a nucleoside or an oligonucleotide region having from 2 to about 10 nucleotides.

4. The inhibitor of DNA methytransferase enzyme according to claim 3 comprising at least one internucleoside linkage selected from the group consisting of phosphodiester, phosphotriester, phosphorothioate, and phosphoramidate linkages, or combinations thereof.

5. The inhibitor of DNA methytransferase enzyme according to claim 3 comprising at least one phosphorothioate internucleoside linkage.

6. The inhibitor of DNA methyltransferase enzyme according to claim 1, having the sequence selected from the group consisting of SEQ. ID. NO. 1, SEQ. ID. NO. 2, SEQ. ID. NO. 3, SEQ. ID. NO. 4, SEQ. ID. NO. 5, SEQ. ID. NO. 6, SEQ. ID. NO. 7, SEQ. ID. NO. 8, SEQ. ID. NO. 9, SEQ. ID. NO. 10, SEQ. ID. NO. 11, SEQ. ID. NO. 12, SEQ. ID. NO. 13, SEQ. ID. NO. 14, SEQ. ID. NO. 15, SEQ. ID. NO. 16, SEQ. ID. NO. 17, SEQ. ID. NO. 18, SEQ. ID. NO. 19, SEQ. ID. NO. 20, SEQ. ID. NO. 21, SEQ. ID. NO. 22, SEQ. ID. NO. 23, SEQ. ID. NO. 24, SEQ. ID. NO. 25, SEQ. ID. NO. 26, SEQ. ID. NO. 27, SEQ. ID. NO. 28, SEQ. ID. NO. 29, SEQ. ID. is NO. 30, SEQ. ID. NO. 31, SEQ. ID. NO. 32, SEQ. ID. NO- 33, SEQ. ID. NO. 34, SEQ. ID. NO. 35, SEQ. ID. NO. 36, SEQ. ID. NO. 37, SEQ. ID. NO. 38, SEQ. ID. NO. 39, SEQ. ID. NO. 40 and SEQ. ID. NO. 41, wherein C is cytidine, T is thymidine, A is adenosine, G is guanine, m is a methyl group at the 5-position of cytosine, B is cytosine, inosine, uridine, 5-bromocytidine, or 5-fluorouridine, X is any base and F is 5-fluorocytosine.

7. An inhibitor of DNA methytransferase enzyme having the general structure

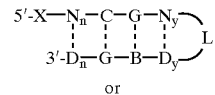

or

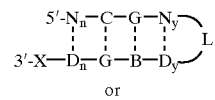

or

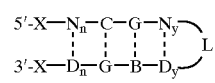

wherein each N is independently any nucleotide, n is a number from 0–20, C is 5-methylcytidine, G is guanidine, y is a number from 0–20, L is a linker, each D is a nucleotide that is complementary to an N such that Watson-Crick base pairing takes place between that D and the N such that the $N_n$-C-G-$N_y$ and the $D_n$-G-B-$D_y$ form a double helix, B is cytosine, inosine, uridine, 5-bromocytosine, abasic deoxyribose, or 5-fluorocytosine, dotted lines between nucleotides represent hydrogen bonding between the nucleotides, B and G are linked by a phosphorothioate or phosphorodithioate linkage and the total number of nucleotides ranges from about 10 to about 50, X is an antisense oligonucleotide of from about 10 to about 50 nucleotides in length, which is complementary to a portion of an RNA encoding DNA MTase enzyme, and L can optionally be X.

8. A diagnostic method for determining whether a particular sample of cells is cancerous, the method comprising preparing an extract from the cells in the cell sample, adding a labeled inhibitor according to claim 2, measuring the extent of formation of a complex between the labeled inhibitor and DNA MTase enzyme, normalizing the level of such complex formation to the number of cells represented in the sample to obtain a normalized complex formation value, and comparing the normalized complex formation value to a normalized complex formation value for non-cancerous and/ or cancerous cell samples.

9. The method according to claim 8, wherein the extract is a nuclear extract.

* * * * *

SEQUENCE LISTING

```
<160> NUMBER OF SEQ ID NOS: 41

<210> SEQ ID NO 1
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a methyl group at the 5-position of
      nucleotides 6 & 11 of the cytosine portion of
      cytidine.
<220> FEATURE:
<221> NAME/KEY: misc_feature
<222> LOCATION: (1)..(21)
<223> OTHER INFORMATION: Nucleotide 21 is n wherein n = u and u =
      uridine.
<220> FEATURE:
<223> OTHER INFORMATION: Description of Artificial Sequence:synthetic
      construct

<400> SEQUENCE: 1
ctgaacggat cgtttcgatc ngttcag                                         27

<210> SEQ ID NO 2
<211> LENGTH: 27
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Nucleotide 21 is n wherein n = i and i =
      inosine.
<220> FEATURE:
<223> OTHER INFORMATION: Description of Artificial Sequence:synthetic
      construct
<220> FEATURE:
<221> NAME/KEY: misc_feature
<222> LOCATION: (1)..(27)
<223> OTHER INFORMATION: Nucleotides 1-27 contain c, t, a and g wherein
      c=cytidine; t=thymidine; a=adenosine; g=guanosine;
      m is a methyl group at the 5-position of
      nucleotides 6 & 11 of the cytosine portion of
      cytidine.

<400> SEQUENCE: 2
ctgaacggat cgtttcgatc ngttcag                                         27

<210> SEQ ID NO 3
<211> LENGTH: 27
<212> TYPE: DNA
```

```
<213> ORGANISM: Artificial Sequence
<220> FEATURE:
<221> NAME/KEY: misc_feature
<222> LOCATION: (1)..(21)
<223> OTHER INFORMATION: Nucleotide 21 is n wherein n = u and u =
      uridine.
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a methyl group at the 5-position of
      nucleotide 6 of the cytosine portion of cytidine.
<220> FEATURE:
<223> OTHER INFORMATION: Description of Artificial Sequence:synthetic
      construct

<400> SEQUENCE: 3
ctgaacggat cgtttcgatc ngttcag                                      27

<210> SEQ ID NO 4
<211> LENGTH: 27
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Nucleotide 21 is n wherein n = i and i =
      inosine.
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a methyl group at the 5-position of
      nucleotide 6 of the cytosine portion of cytidine.
<220> FEATURE:
<223> OTHER INFORMATION: Description of Artificial Sequence:synthetic
      construct

<400> SEQUENCE: 4
ctgaacggat cgtttcgatc ngttcag                                      27

<210> SEQ ID NO 5
<211> LENGTH: 15
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Nucleotide 14 is n wherein n = i and i =
      inosine.
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine.
<220> FEATURE:
<221> NAME/KEY: misc_feature
<222> LOCATION: (1)..(15)
<223> OTHER INFORMATION: m is a methyl group at the 5-position of
      nucleotides 1, 5 and 10 of the cytosine portion of cytidine.
<220> FEATURE:
<223> OTHER INFORMATION: Description of Artificial Sequence:synthetic
      construct

<400> SEQUENCE: 5
cgaacgtttc gttng                                                   15

<210> SEQ ID NO 6
<211> LENGTH: 15
<212> TYPE: DNA
<213> ORGANISM: Artificial Sequence
```

```
<220> FEATURE:
<221> NAME/KEY: misc_feature
<222> LOCATION: (1)..(14)
<223> OTHER INFORMATION: Nucleotide 14 is n wherein n = i and i =
      inosine.
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<223> OTHER INFORMATION: Description of Artificial Sequence:synthetic
      construct

<400> SEQUENCE: 6
cgaacgtttc gttng                                                    15

<210> SEQ ID NO 7
<211> LENGTH: 15
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Nucleotide 14 is n wherein n = i and i =
      inosine.
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine;
      m is a methyl group at the 5-position of
      nucleotide 1 of the cytosine portion of cytidine.
<220> FEATURE:
<223> OTHER INFORMATION: Description of Artificial Sequence:synthetic
      construct

<400> SEQUENCE: 7
cgaacgtttc gttng                                                    15

<210> SEQ ID NO 8
<211> LENGTH: 15
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Nucleotide 14 is n wherein n = u and u =
      uridine.
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine.
<220> FEATURE:
<221> NAME/KEY: misc_feature
<222> LOCATION: (1)..(15)
<223> OTHER INFORMATION: m is a methyl group at the 5-position of
      nucleotides 1, 5 and 10 of the cytosine portion of cytidine.
<220> FEATURE:
<223> OTHER INFORMATION: Description of Artificial Sequence:synthetic
      construct

<400> SEQUENCE: 8
cgaacgtttc gttng                                                    15

<210> SEQ ID NO 9
<211> LENGTH: 15
<212> TYPE: DNA
<213> ORGANISM: Artificial Sequence
```

```
<220> FEATURE:
<221> NAME/KEY: misc_feature
<222> LOCATION: (1)..(14)
<223> OTHER INFORMATION: Nucleotide 14 is n wherein n= u and u =
      uridine.
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<223> OTHER INFORMATION: Description of Artificial Sequence:synthetic
      construct

<400> SEQUENCE: 9
cgaacgtttc gttng                                                      15

<210> SEQ ID NO 10
<211> LENGTH: 15
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Nucleotide 14 is n wherein n = u and u =
      uridine.
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine;
      m is a methyl group at the 5-position of
      nucleotide 1 of the cytosine portion of cytidine.
<220> FEATURE:
<223> OTHER INFORMATION: Description of Artificial Sequence:synthetic
      construct

<400> SEQUENCE: 10
cgaacgtttc gttng                                                      15

<210> SEQ ID NO 11
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine;
      m is a methyl group at the 5-position of
      nucleotide 6 of the cytosine portion of cytidine.
<220> FEATURE:
<221> NAME/KEY: misc_feature
<222> LOCATION: (1)..(14)
<223> OTHER INFORMATION: Nucleotide 14 is n wherein n = b and b =
      cytosine,
      inosine, uridine, 5-bromocytidine or 5-fluorouridine.
<220> FEATURE:
<223> OTHER INFORMATION: Description of Artificial Sequence:synthetic
      construct

<400> SEQUENCE: 11
ctgaacgcga aagng                                                      15

<210> SEQ ID NO 12
<211> LENGTH: 27
<212> TYPE: DNA
<213> ORGANISM: Artificial Sequence
<220> FEATURE:
<221> NAME/KEY: misc_feature
```

```
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a methyl group at the 5-position of
      nucleotides 6 & 11 of the cytosine portion of
      cytidine.
<220> FEATURE:
<221> NAME/KEY: misc_feature
<222> LOCATION: (1)..(21)
<223> OTHER INFORMATION: Nucleotides 16 and 21 are n wherein n = b and
      b = cytosine, inosine, uridine, 5-bromocytidine or
      5-fluorouridine.
<220> FEATURE:
<223> OTHER INFORMATION: Description of Artificial Sequence:synthetic
      construct

<400> SEQUENCE: 12
ctgaacggat cgtttngatc ngttcag                                              27

<210> SEQ ID NO 13
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t-thymidine; a=adenosine; g=guanosine;
      m is a methyl group at the 5-position of
      nucleotides 6 & 11 of the cytosine portion of
      cytidine.
<220> FEATURE:
<223> OTHER INFORMATION: Description of Artificial Sequence:synthetic
      construct

<400> SEQUENCE: 13
ctgaacggat cgtttcgatc cgttcag                                              27

<210> SEQ ID NO 14
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a methyl group at the 5-position of
      nucleotides 6 & 11 of the cytosine portion of
      cytidine.
<220> FEATURE:
<221> NAME/KEY: misc_feature
<222> LOCATION: (1)..(21)
<223> OTHER INFORMATION: Nucleotides 16 & 21 are n wherein n is f and
      f = 5-fluorocytosine.
<220> FEATURE:
<223> OTHER INFORMATION: Description of Artificial Sequence:synthetic
      construct

<400> SEQUENCE: 14
ctgaacggat cgtttngatc ngttcag                                              27

<210> SEQ ID NO 15
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a methyl group at the 5-position of
      nucleotide 6 of the cytosine portion of cytidine.
```

```
<220> FEATURE:
<223> OTHER INFORMATION: Description of Artificial Sequence:synthetic
      construct

<400> SEQUENCE: 15
ctgaacggat tgtttcgatc cgttcag                                             27

<210> SEQ ID NO 16
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a methyl group at the 5-position of
      nucleotides 6 & 11 of the cytosine portion of
      cytidine.
<220> FEATURE:
<221> NAME/KEY: misc_feature
<222> LOCATION: (1)..(21)
<223> OTHER INFORMATION: Nucleotide 21 is n wherein n is x and x = any
      base.
<220> FEATURE:
<223> OTHER INFORMATION: Description of Artificial Sequence:synthetic
      construct

<400> SEQUENCE: 16
ctgaacggat cgtttcgatc ngttcag                                             27

<210> SEQ ID NO 17
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a methyl group at the 5-position of
      nucleotides 2, 6 & 11 of the cytosine portion of
      cytidine.
<220> FEATURE:
<221> NAME/KEY: misc_feature
<222> LOCATION: (1)..(21)
<223> OTHER INFORMATION: Nucleotides 16 & 21 are n wherein n = i and i =
      inosine.
<220> FEATURE:
<223> OTHER INFORMATION: Description of Artificial Sequence:synthetic
      construct

<400> SEQUENCE: 17
tcgaacggat cgtttngatc ngttcga                                             27

<210> SEQ ID NO 18
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine;
      m is a mehtyl group at the 5-position of
      nucleotides 2, 6 & 11 of the cytosine portion of
      cytidine.
<220> FEATURE:
<221> NAME/KEY: misc_feature
<222> LOCATION: (1)..(26)
<223> OTHER INFORMATION: Nucleotides 16, 21 & 26 are n wherein n = i and
      i =  inosine.
<220> FEATURE:
```

```
<223> OTHER INFORMATION: Description of Artificial Sequence:synthetic
      construct

<400> SEQUENCE: 18
tcgaacggat cgtttngatc ngttcna                                         27

<210> SEQ ID NO 19
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t-thymidine; a-adenosine; g=guanosine;
      m is a methyl group at the 5-position of
      nucleotide 6 of the cytosine portion of cytidine.
<220> FEATURE:
<221> NAME/KEY: misc_feature
<222> LOCATION: (1)..(14)
<223> OTHER INFORMATION: Nucleotide 14 is n wherein n = b and b =
      cytosine, inosine, uridine, 5-bromocytidine or 5-fluorouridine.
<220> FEATURE:
<223> OTHER INFORMATION: Description of Artificial Sequence:synthetic
      construct

<400> SEQUENCE: 19
ctgaacgcga aagng                                                      15

<210> SEQ ID NO 20
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Nucleotides 1-17 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<223> OTHER INFORMATION: Description of Artificial Sequence:synthetic
      construct

<400> SEQUENCE: 20
cgaacgtttt tcgttcg                                                    17

<210> SEQ ID NO 21
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Nucleotides 1-17 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<221> NAME/KEY: misc_feature
<222> LOCATION: (1)..(16)
<223> OTHER INFORMATION: Nucleotide 16 is n wherein n = i and i =
      inosine.
<220> FEATURE:
<223> OTHER INFORMATION: Description of Artificial Sequence:synthetic
      construct

<400> SEQUENCE: 21
cgaacgtttt tcgttng                                                    17
```

```
<210> SEQ ID NO 22
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Nucleotides 1-17 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<221> NAME/KEY: misc_feature
<222> LOCATION: (1)..(16)
<223> OTHER INFORMATION: Nucleotide 16 is n wherein n = u and u =
      uridine.
<220> FEATURE:
<223> OTHER INFORMATION: Description of Artificial Sequence:synthetic
      construct

<400> SEQUENCE: 22
cgaacgtttt tcgttng                                                     17

<210> SEQ ID NO 23
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Nucleotides 1-17 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<221> NAME/KEY: misc_feature
<222> LOCATION: (1)..(16)
<223> OTHER INFORMATION: Nucleotides 12 & 16 are n wherein n = f and f =
      5-fluorocytosine.
<220> FEATURE:
<223> OTHER INFORMATION: Description of Artificial Sequence:synthetic
      construct

<400> SEQUENCE: 23
cgaacgtttt tngttng                                                     17

<210> SEQ ID NO 24
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Nucleotides 1-17 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<221> NAME/KEY: misc_feature
<222> LOCATION: (1)..(16)
<223> OTHER INFORMATION: Nucleotides 12 & 16 are n wherein n = b and b =
      cytosine, inosine, uridine, 5-bromocytidine or
      5-fluorouridine.
<220> FEATURE:
<223> OTHER INFORMATION: Description of Artificial Sequence:synthetic
      construct

<400> SEQUENCE: 24
cgaacgtttt tngttng                                                     17
```

```
<210> SEQ ID NO 25
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Nucleotides 1-30 contain c, t, a & g wherein
      c=cytidine; t=thymidine; a=adenosine; g=guanosine;
      m is a methyl group at the 5-position of
      nucleotide 21 of the cytosine portion of cytidine.
<220> FEATURE:
<223> OTHER INFORMATION: Description of Artificial Sequence:synthetic
      construct

<400> SEQUENCE: 25
catctgccat tcccactcta cgcgaaagcg                                    30

<210> SEQ ID NO 26
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Nucleotides 1-30 contain c, t, a & g wherein
      c=cytidine; t=thymidine; a=adenosine; g=guanosine;
      m is a methyl group at the 5-position of
      nucleotide 21 of the cytosine portion of cytidine.
<220> FEATURE:
<221> NAME/KEY: misc_feature
<222> LOCATION: (1)..(29)
<223> OTHER INFORMATION: Nucleotide 29 is n wherein n = i and i =
      inosine.
<220> FEATURE:
<223> OTHER INFORMATION: Description of Artificial Sequence:synthetic
      construct

<400> SEQUENCE: 26
catctgccat tcccactcta cgcgaaagng                                    30

<210> SEQ ID NO 27
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Nucleotides 1-30 contain c, t, a & g wherein
      c=cytidine; t=thymidine; a=adenosine; g=guanosine;
      m is a methyl group at the 5-position of
      nucleotide 21 of the cytosine portion of cytidine.
<220> FEATURE:
<221> NAME/KEY: misc_feature
<222> LOCATION: (1)..(29)
<223> OTHER INFORMATION: Nucleotide 29 is n wherein n = u and u =
      uridine.
<220> FEATURE:
<223> OTHER INFORMATION: Description of Artificial Sequence:synthetic
      construct

<400> SEQUENCE: 27
catctgccat tcccactcta cgcgaaagng                                    30

<210> SEQ ID NO 28
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Nucleotides 1-30 contain c, t, a & g wherein
```

```
      c=cytidine; t=thymidine; a=adenosine; g=guanosine;
      m is a methyl group at the 5-position of
      nucleotide 21 of the cytosine portion of cytidine.
<220> FEATURE:
<221> NAME/KEY: misc_feature
<222> LOCATION: (1)..(29)
<223> OTHER INFORMATION: Nucleotide 29 is n wherein n = f and f =
      5-fluorocytosine.
<220> FEATURE:
<223> OTHER INFORMATION: Description of Artificial Sequence:synthetic
      construct

<400> SEQUENCE: 28
catctgccat tcccactcta cgcgaaagng                                         30

<210> SEQ ID NO 29
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Nucleotides 1-30 contain c, t, a & g wherein
      c=cytidine; t=thymidine; a=adenosine; g=guanosine;
      m is a methyl group at the 5-position of
      nucleotide 21 of the cytosine portion of cytidine.
<220> FEATURE:
<221> NAME/KEY: misc_feature
<222> LOCATION: (1)..(29)
<223> OTHER INFORMATION: Nucleotide 29 is n wherein n = b and b =
      cytosine, inosine, uridine, 5-bromocytidine or 5-fluorouridine.
<220> FEATURE:
<223> OTHER INFORMATION: Description of Artificial Sequence:synthetic
      construct

<400> SEQUENCE: 29
catctgccat tcccactcta cgcgaaagng                                         30

<210> SEQ ID NO 30
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Nucleotides 1-30 contain c, t, a & g wherein
      c=cytidine; t=thymidine; a=adenosine; g=guanosine;
      m is a methyl group at the 5-position of
      nucleotide 21 of the cytosine portion of cytidine.
<220> FEATURE:
<221> NAME/KEY: misc_feature
<222> LOCATION: (1)..(29)
<223> OTHER INFORMATION: Nucleotide 29 is n wherein n = i and i =
      inosine.
<220> FEATURE:
<223> OTHER INFORMATION: Description of Artificial Sequence:synthetic
      construct

<400> SEQUENCE: 30
catctgccat tcccactcta cgcgaaagng                                         30

<210> SEQ ID NO 31
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t-thymidine; a-adenosine; g-guanosine;
      m is a methyl group at the 5-position of
      nucleotide 6 of the cytosine portion of cytidine.
<220> FEATURE:
```

<223> OTHER INFORMATION: Description of Artificial Sequence:synthetic
      construct

<400> SEQUENCE: 31
ctgaacgcga aagcg                                                    15

<210> SEQ ID NO 32
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine;
      m is a methyl group at the 5-position of
      nucleotide 6 of the cytosine portion of cytidine.
<220> FEATURE:
<221> NAME/KEY: misc_feature
<222> LOCATION: (1)..(14)
<223> OTHER INFORMATION: Nucleotide 14 is n wherien n = i and i =
      inosine.
<220> FEATURE:
<223> OTHER INFORMATION: Description of Artificial Sequence:synthetic
      construct

<400> SEQUENCE: 32
ctgaacgcga aagng                                                    15

<210> SEQ ID NO 33
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: Nucleotides 1-15 contain c, t, a & g wherein
      c=cytidine; t=thymidine; a=adenosine; g=guanosine;
      m is a methyl group at the 5-position of
      nucleotide 6 of the cytosine portion of cytidine.
<220> FEATURE:
<221> NAME/KEY: misc_feature
<222> LOCATION: (1)..(14)
<223> OTHER INFORMATION: Nucleotide 14 is n wherein n = u and u =
      uridine.
<220> FEATURE:
<223> OTHER INFORMATION: Description of Artificial Sequence:synthetic
      construct

<400> SEQUENCE: 33
ctgaacgcga aagng                                                    15

<210> SEQ ID NO 34
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine.
<220> FEATURE:
<221> NAME/KEY: misc_feature
<222> LOCATION: (1)..(21)
<223> OTHER INFORMATION: Nucleotide 21 is n wherein n = u and u =
      uridine.
<220> FEATURE:
<223> OTHER INFORMATION: Description of Artificial Sequence:synthetic
      construct

<400> SEQUENCE: 34
ctgaacggat tgtttcgatc ngttcag                                       27

<210> SEQ ID NO 35
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine.
<220> FEATURE:
<221> NAME/KEY: misc_feature
<222> LOCATION: (1)..(27)
<223> OTHER INFORMATION: m is a methyl group at the 5-position of
      nucleotides 6, 11, 16 and 21 of the cytosine portion
      of cytidine.
<220> FEATURE:
<223> OTHER INFORMATION: Description of Artificial Sequence:synthetic
      construct

<400> SEQUENCE: 35
ctgaacggat cgtttcgatc cgttcag                                27

<210> SEQ ID NO 36
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Nucleotides 1-27 contain c, t, a & g wherein
      c=cytidine; t=thymidine; a=adenosine; g=guanosine.
<220> FEATURE:
<223> OTHER INFORMATION: Description of Artificial Sequence:synthetic
      construct

<400> SEQUENCE: 36
ctgaacggat cgtttcgatc cgttcag                                27

<210> SEQ ID NO 37
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Nucleotides 1-16 contain c, t, a & g wherein
      c=cytidine; t=thymidine; a=adenosine; g=guanosine;
      m is a methyl group at the 5-position of
      nucleotides 1 & 5 of the cytosine porition of
      cytidine.
<220> FEATURE:
<223> OTHER INFORMATION: Description of Artificial Sequence:synthetic
      construct

<400> SEQUENCE: 37
cgaacgtttt cgttcg                                            16

<210> SEQ ID NO 38
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Nucleotides 1-16 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<221> NAME/KEY: misc_feature

```
<222> LOCATION: (1)..(15)
<223> OTHER INFORMATION: Nucleotide 15 is n wherein n = i and i =
      inosine.
<220> FEATURE:
<223> OTHER INFORMATION: Description of Artificial Sequence:synthetic
      construct

<400> SEQUENCE: 38
cgaacgtttt cgttng                                              16

<210> SEQ ID NO 39
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Nucleotides 1-16 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<221> NAME/KEY: misc_feature
<222> LOCATION: (1)..(15)
<223> OTHER INFORMATION: Nucleotide 15 is n wherein n = u and u =
      uridine.
<220> FEATURE:
<223> OTHER INFORMATION: Description of Artificial Sequence:synthetic
      construct

<400> SEQUENCE: 39
cgaacgtttt cgttng                                              16

<210> SEQ ID NO 40
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Nucleotides 1-16 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<221> NAME/KEY: misc_feature
<222> LOCATION: (1)..(15)
<223> OTHER INFORMATION: Nucleotide 15 is n wherein n = f and f =
      5-fluorocytosine.
<220> FEATURE:
<223> OTHER INFORMATION: Description of Artificial Sequence:synthetic
      construct

<400> SEQUENCE: 40
cgaacgtttt cgttng                                              16

<210> SEQ ID NO 41
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Nucleotides 1-16 contain c, t, a & g wherein
      c=cytidine; t=thymidine; a=adenosine; g=guanosine;
      m is a methyl group at the 5-position of
      nucleotides 1 & 5 of the cytosine portion of
      cytidine.
<220> FEATURE:
<221> NAME/KEY: misc_feature
<222> LOCATION: (1)..(15)
```

-continued

```
<223> OTHER INFORMATION: Nucleotide 15 is n wherein n = b and b =
      cytosine, inosine, uridine, 5-bromocytidine or 5-fluorouridine.
<220> FEATURE:
<223> OTHER INFORMATION: Description of Artificial Sequence:synthetic
      construct

<400> SEQUENCE: 41
cgaacgtttt cgttng                                                      16
```